(12) United States Patent
Florescu et al.

(10) Patent No.: US 10,794,902 B2
(45) Date of Patent: Oct. 6, 2020

(54) DIGITAL CONTROL OF ON-CHIP MAGNETIC PARTICLE ASSAY

(71) Applicant: Silicon BioDevices, Inc., Palo Alto, CA (US)

(72) Inventors: Octavian Florescu, Berkeley, CA (US); Daniel Wong, Sunnyvale, CA (US); Tracie Martin, Oakland, CA (US); Duane Yamasaki, El Cerrito, CA (US); Remy Cromer, Saratoga, CA (US)

(73) Assignee: Silicon BioDevices, Inc., Pleasanton, CA (US)

( * ) Notice: Subject to any disclaimer, the term of this patent is extended or adjusted under 35 U.S.C. 154(b) by 571 days.

(21) Appl. No.: 15/456,049

(22) Filed: Mar. 10, 2017

(65) Prior Publication Data

US 2017/0184579 A1    Jun. 29, 2017

Related U.S. Application Data

(60) Division of application No. 14/942,903, filed on Nov. 16, 2015, now abandoned, which is a continuation of
(Continued)

(51) Int. Cl.
*G01N 33/543* (2006.01)
*B01L 3/00* (2006.01)
(Continued)

(52) U.S. Cl.
CPC .. *G01N 33/54326* (2013.01); *B01L 3/502761* (2013.01); *B01L 3/561* (2013.01); *C12Q 1/686* (2013.01); *G01N 21/255* (2013.01); *G01N 21/82* (2013.01); *G01N 27/745* (2013.01); *G06K 19/06028* (2013.01); *G06K 19/06037* (2013.01); *B01L 2200/0605* (2013.01); *B01L 2200/0668* (2013.01); *B01L 2200/148* (2013.01); *B01L 2200/16* (2013.01); *B01L 2300/023* (2013.01);
(Continued)

(58) Field of Classification Search
CPC .................. G01N 21/82; G01N 21/255; G01N 2201/061; G01N 2201/068; G01N 27/745; G01N 33/54326; B01L 3/502761; B01L 2200/148; B01L 2200/16; B01L 2300/0874; B01L 2400/0406; B01L 2400/043; B01L 2200/0668; B01L 2300/0838; B01L 2300/0636; B01L 2200/0605; B01L 3/5612; B01L 2300/12; B01L 2300/027; B01L 2300/023; G16H 50/20; G06K 19/06028; G06F 21/602; C12Q 1/686; Y02A 90/26
See application file for complete search history.

(56) References Cited

U.S. PATENT DOCUMENTS 3,505,173 A    4/1970 Randell
4,188,537 A    2/1980 Franke
(Continued)

FOREIGN PATENT DOCUMENTS

WO    WO 2012/048288    4/2012
WO    WO 2014/189624    11/2014

*Primary Examiner* — Shogo Sasaki
(74) *Attorney, Agent, or Firm* — Levine Bagade Han LLP

(57) ABSTRACT

An assay system and method for use in the field of chemical testing is disclosed. The assay system can be used for filtering whole blood for testing on an integrated circuit containing digital control functionality.

14 Claims, 21 Drawing Sheets

Related U.S. Application Data application No. PCT/US2014/033607, filed on Apr. 10, 2014.

(60) Provisional application No. 61/891,319, filed on Oct. 15, 2013, provisional application No. 61/825,464, filed on May 20, 2013.

(51) Int. Cl.
  *G01N 21/82* (2006.01)
  *G01N 27/74* (2006.01)
  *G01N 21/25* (2006.01)
  *C12Q 1/686* (2018.01)
  *G06K 19/06* (2006.01)
  *G16H 50/20* (2018.01)
  *G06F 21/60* (2013.01)

(52) U.S. Cl.
  CPC . *B01L 2300/027* (2013.01); *B01L 2300/0636* (2013.01); *B01L 2300/0838* (2013.01); *B01L 2300/0874* (2013.01); *B01L 2300/12* (2013.01); *B01L 2400/043* (2013.01); *B01L 2400/0406* (2013.01); *G01N 2201/061* (2013.01); *G01N 2201/068* (2013.01); *G06F 21/602* (2013.01); *G16H 50/20* (2018.01); *Y02A 90/26* (2018.01)

(56) References Cited

U.S. PATENT DOCUMENTS

| | | | |
|---|---|---|---|
| 8,843,382 B2 * | 9/2014 | Kim | G06Q 10/10 705/2 |
| 9,579,655 B2 * | 2/2017 | DeJohn | C12Q 1/686 |
| 10,436,773 B2 * | 10/2019 | Depa | G01N 21/8483 |
| 2005/0033196 A1 * | 2/2005 | Alroy | A61B 5/150022 600/573 |
| 2005/0203353 A1 * | 9/2005 | Ma | G01N 21/01 600/315 |
| 2006/0100938 A1 * | 5/2006 | Fukuma | G02C 13/003 382/118 |
| 2006/0222567 A1 * | 10/2006 | Kloepfer | G01N 21/8483 422/68.1 |
| 2006/0230072 A1 | 10/2006 | Partovi et al. | |
| 2011/0071055 A1 | 3/2011 | Belgrader et al. | |
| 2016/0139035 A1 | 5/2016 | Florescu et al. | |
| 2017/0286636 A1 * | 10/2017 | Sobie | G06Q 50/24 |

* cited by examiner

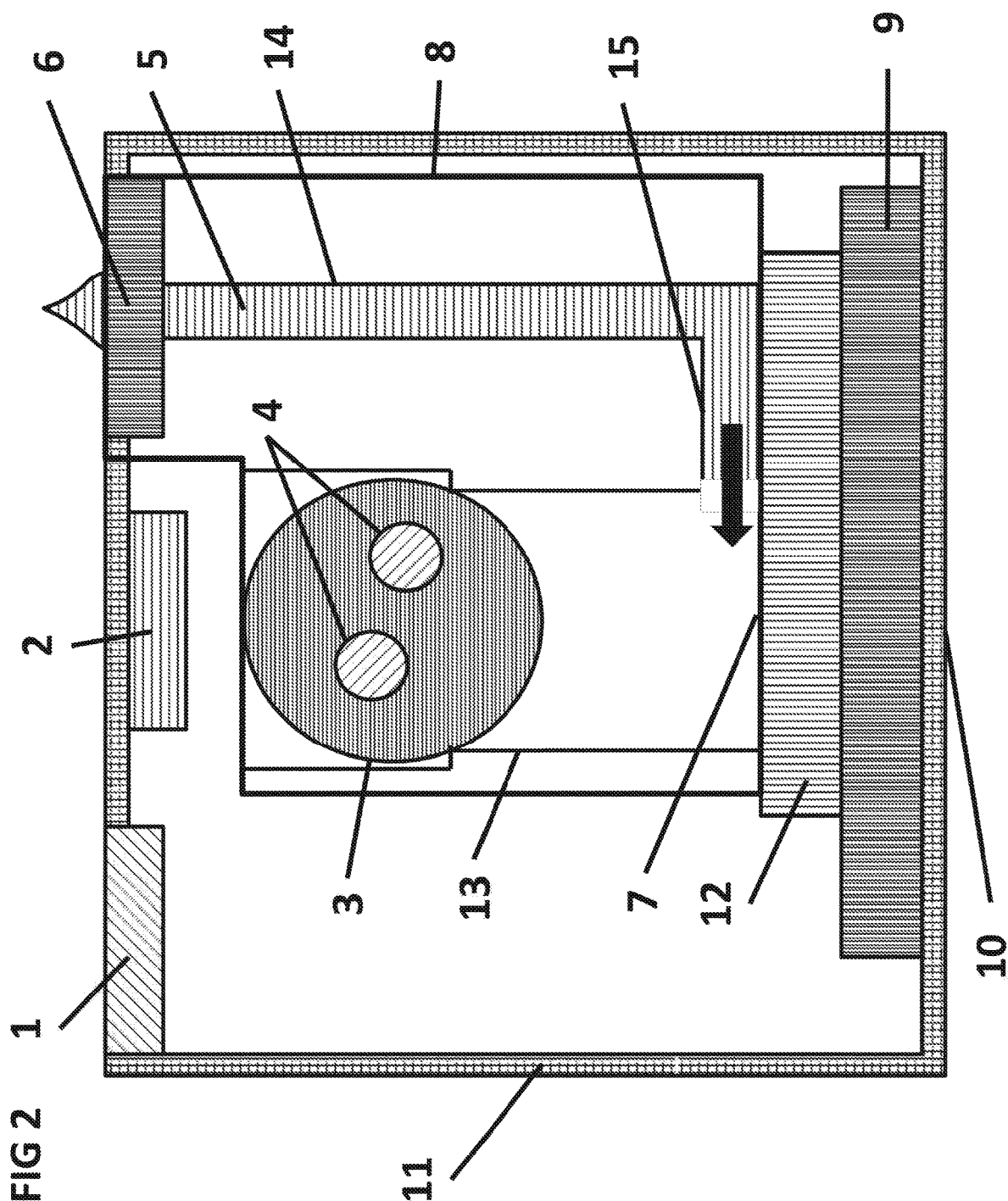

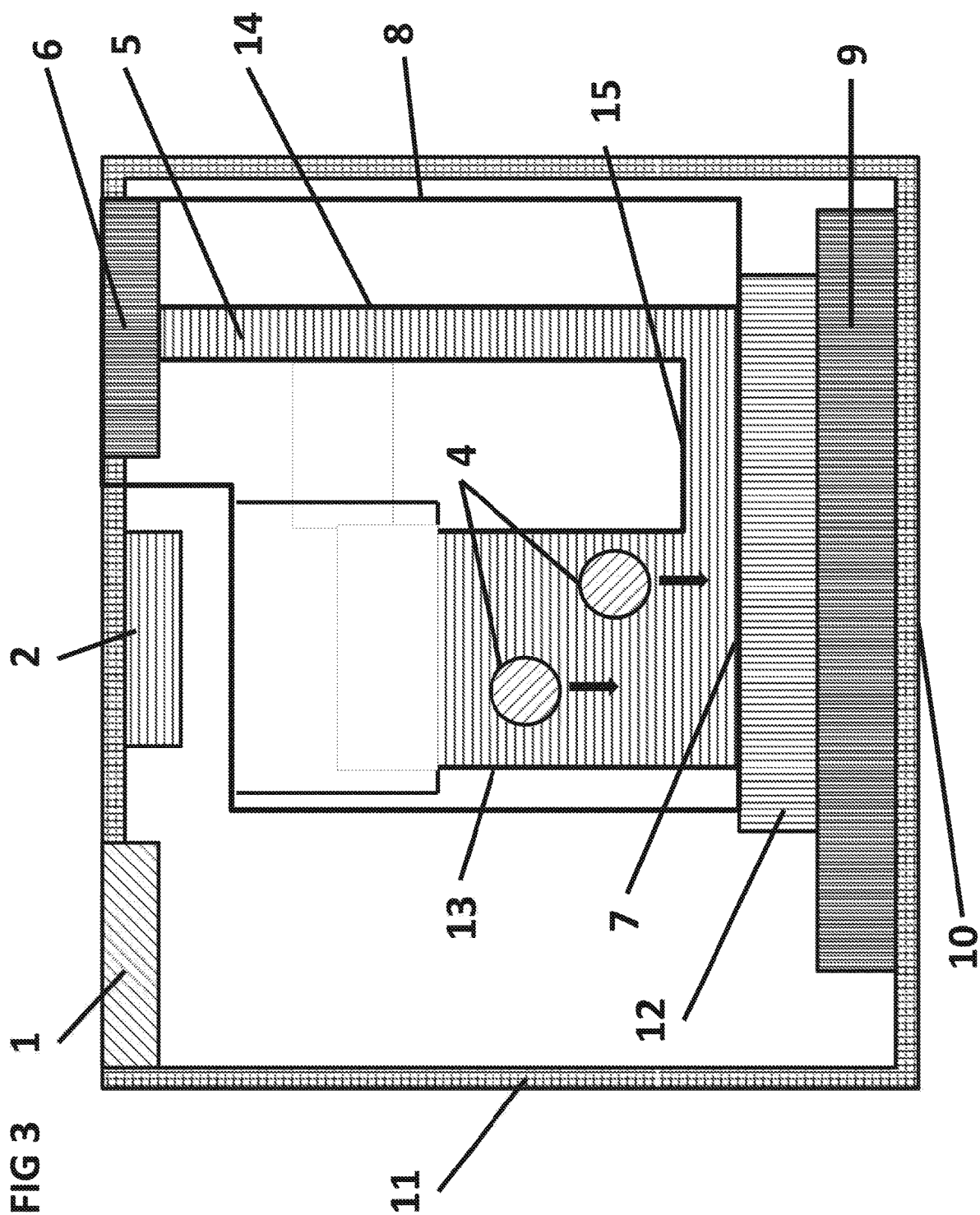

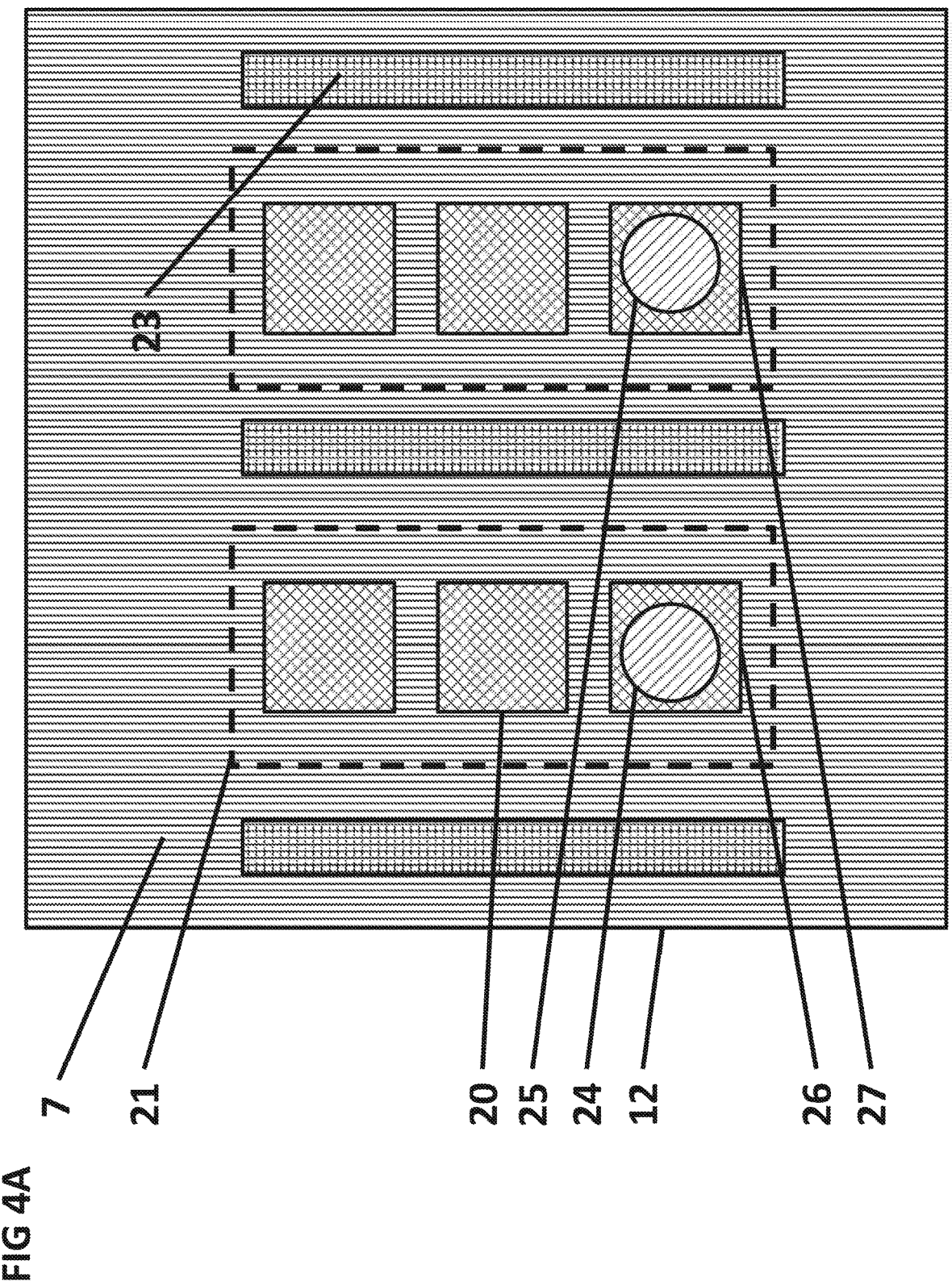

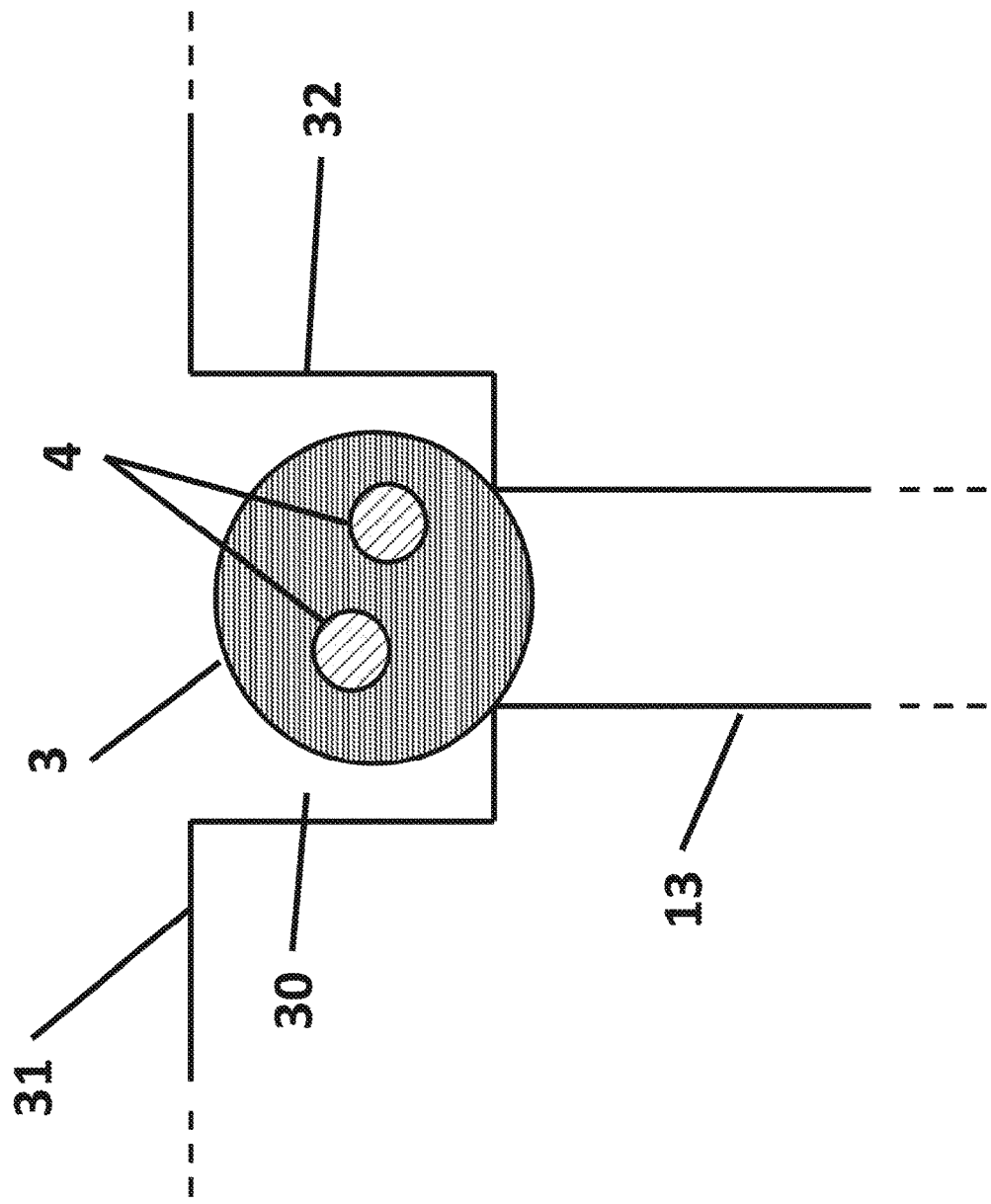

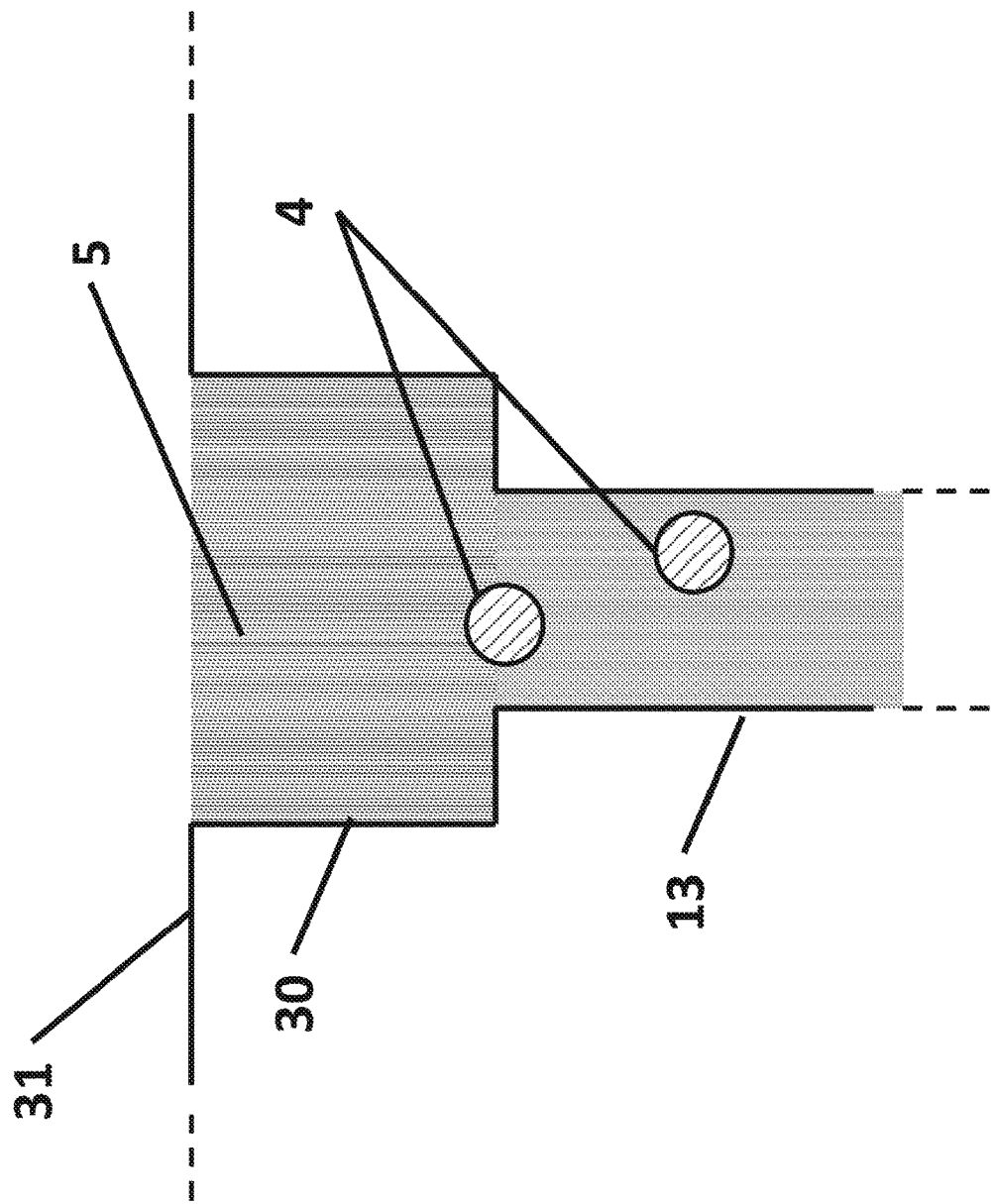

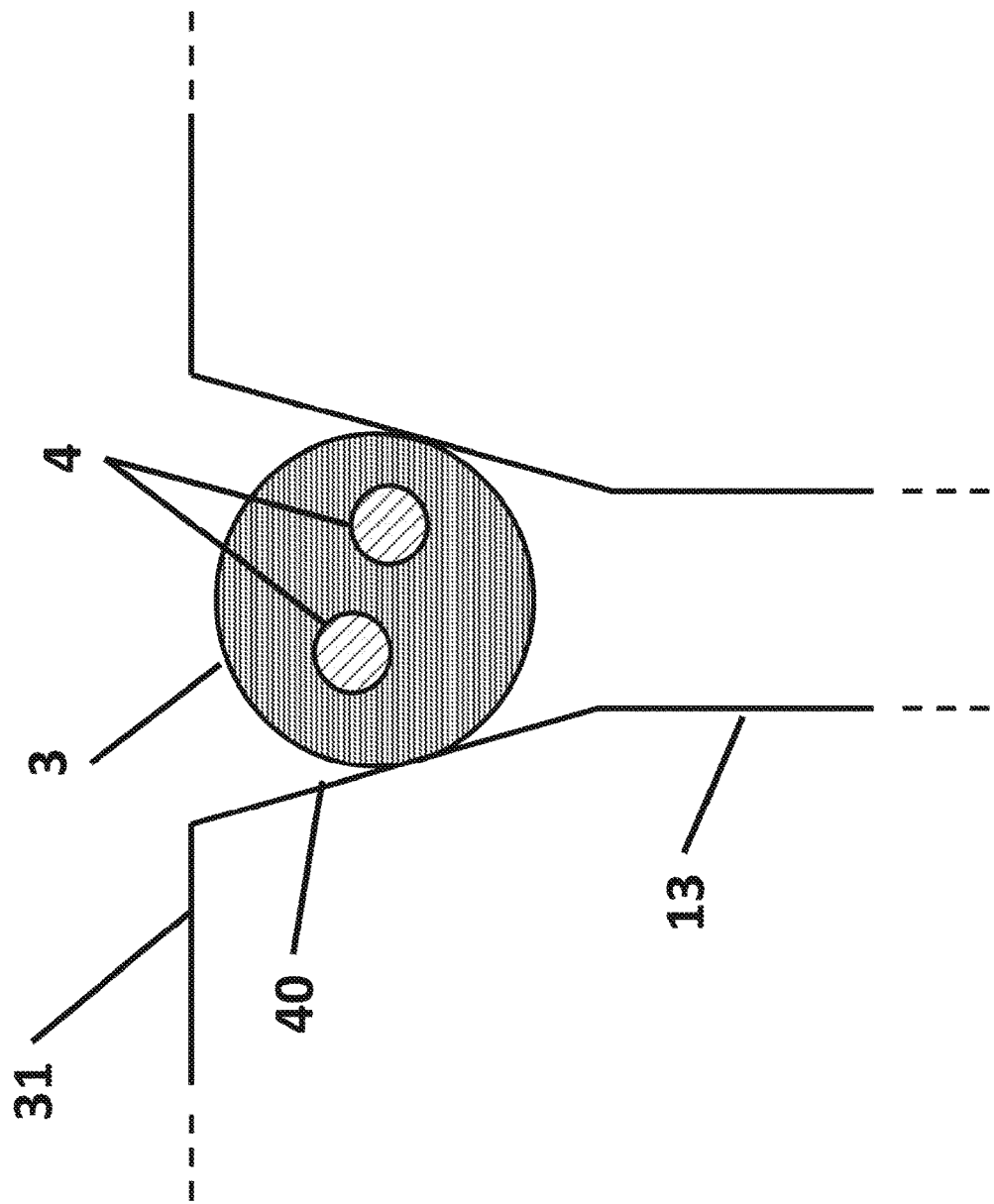

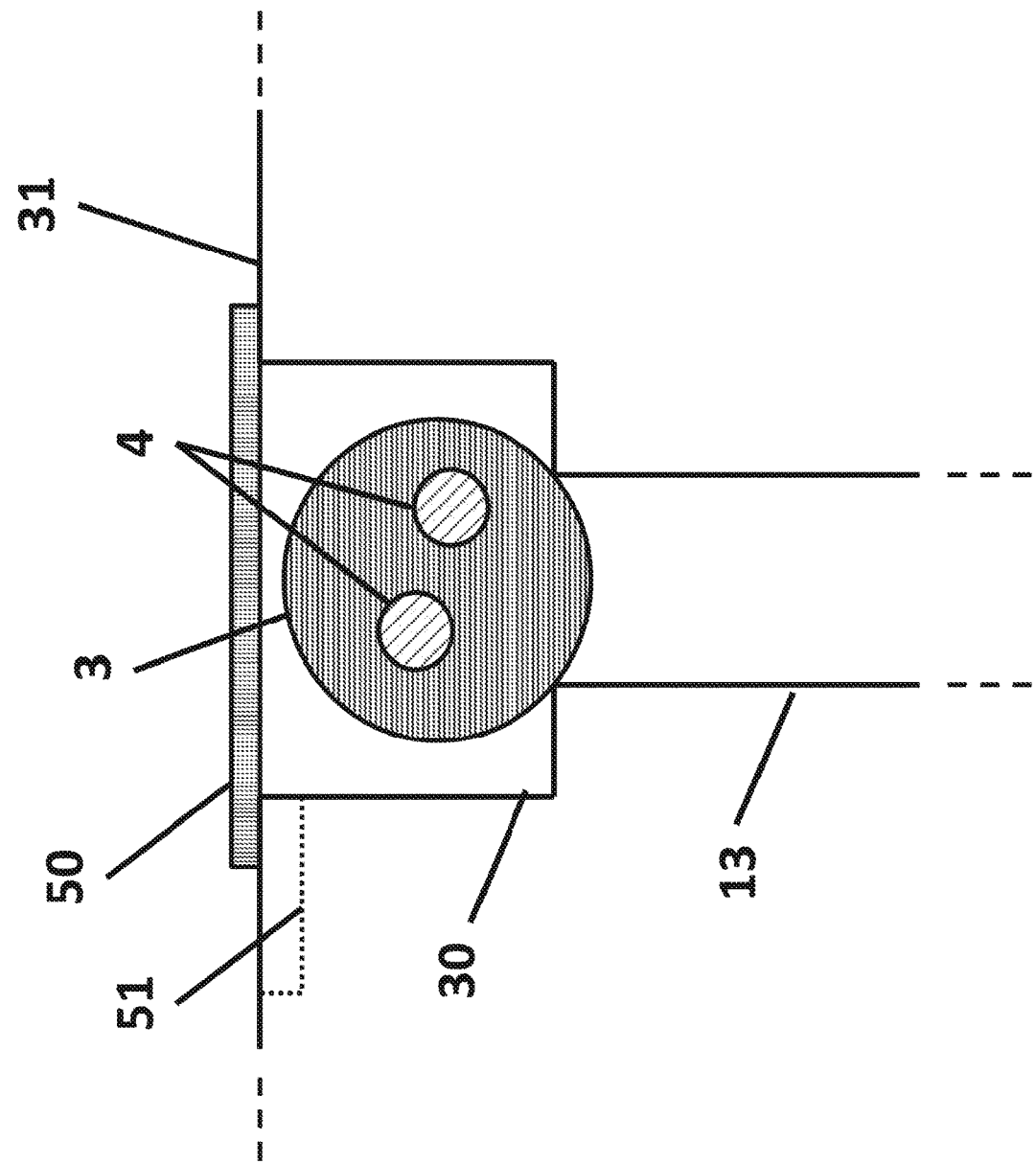

DIGITAL CONTROL OF ON-CHIP MAGNETIC PARTICLE ASSAY

CROSS-REFERENCE TO RELATED APPLICATIONS

The present application is a divisional of U.S. patent application Ser. No. 14/942,903, filed Nov. 16, 2015, now abandoned, which is a continuation of PCT International Application No. PCT/US2014/033607, filed Apr. 10, 2014, which claims priority to U.S. Provisional Application No. 61/825,464, filed May 20, 2013; and U.S. Provisional Application No. 61/891,319, filed Oct. 15, 2013, each of which are incorporated herein by reference in their entireties.

BACKGROUND

1. Technical Field

An assay system and method for use in the field of chemical testing is disclosed. More particularly, the assay system can be used for filtering whole blood for testing on an integrated circuit containing digital control functionality.

2. Summary of the Related Art

Point-of-Care (POC) diagnostic medical devices facilitate early stage detection of diseases, enable more individually tailored therapies, and allow doctors to follow up with patients more easily to see if prescribed treatments are working. To ensure widespread adoption, these tools must be accurate, easy to use by untrained individuals, and inexpensive to produce and distribute. Immuno-Assay (IA) applications are particularly well-suited for the POC since a wide range of conditions, from cardiovascular disease to cancer to communicable infections, can be identified from soluble protein bio-markers. The detection and quantitation of these bio-markers from raw samples such as whole blood often involves labeling the target protein using fluorescent or phosphorescent molecules, enzymes, quantum dots, metal particles or magnetic particles. For high sensitivity applications, the labels specifically bound to the target analytes must be distinguished from the unbound ones that contribute to background noise. By combining both label separation and detection in a low cost, easy to use format, the Immuno-Chromatographic Test (ICT) achieves stand-alone operation, i.e. the ability to perform an assay without necessitating an electronic reader or an external sample preparation system. Stand-alone operation is an often overlooked attribute, but one that is key to the popularity of ICTs, achieved despite other drawbacks such as low biochemical sensitivity, user interpretation, inaccurate quantitation, timing requirements, and awkward multiplexing.

The use of magnetic particle labeling is ideal for POC applications; magnetic particles can be individually detected, so sub-pico molar sensitivities can be achieved without signal amplification steps that can take up to an hour as in case of enzymatic labeling. Also, by micro-arraying the sensing areasensing areas onto which the particles bind, multiplexed operation can be achieved at low cost. The use of magnetic particles can reduce incubation times, since they can bind to the target analytes with solution-phase kinetics due to their high surface area to volume ratio. Furthermore, the ability to pull the magnetic particles out of solution magnetically and gravitationally overcomes the slow diffusion processes that plague most high sensitivity protocols. The signals from magnetic particles can be stable over time, insensitive to changes in temperature or chemistries and detected in opaque or translucent solutions like whole blood or plasma. The biological magnetic background signal can be low, so high assay sensitivity can be achieved with minimal sample preparation. Most importantly, the use of magnetic particles as assay labels can permit stand-alone device operation, since these particles can be both manipulated and detected electromagnetically.

"Magnetic particles" are nano-meter or micro-meter sized particles that display magnetic, diamagnetic, ferromagnetic, ferrimagnetic, paramagnetic, super-paramagnetic or antiferromagnetic behavior. "Magnetic particles" can refer to individual particles or larger aggregates of particles such as magnetic beads.

Magnetic particle sensors are sensor embedded in an integrated circuit that can detect magnetic particles. Examples include optical sensors, magnetic sensors, capacitive sensors, inductive sensors, pressure sensors.

ICTs in which magnetic particles are used as the assay labels are an improvement to conventional ICTs since the detection of the particles is not limited to the surface of the strip, but can be performed throughout the volume of the strip, resulting in higher sensitivities and improved quantitative accuracy. However, volumetric detection of magnetic particles cannot be readily integrated in a stand-alone device, so these implementations require an external device to measure the volume magnetization in the strip.

One alternative for integration into a stand-alone assay system is to use magnetic particles that bind to the target analytes in solution before sedimenting via gravity or magnetic force to sensing areas where the specifically bound particles can be detected. A bio-functionalized IC can be used to detect the specifically bound particles. However, most IC-based immuno-assay implementations reported to date cannot operate stand-alone since they require either off-chip components for particle detection, or micro-fluidic actuation for particle manipulation and sample preparation. Other implementations simply cannot reach the cost structures necessary to compete in the current marketplace.

For POC application, it is desirable that the sample preparation be rapid since the assay is limited to 10-15 minutes. In addition, to obviate the need for refrigeration equipment and to facilitate storage and distribution, a dry sample preparation system is desired. It is also desirable to have a sample preparation system that receives small unprocessed samples from patients. The average hanging drop of blood from a finger stick yields approximately 15 µl of fluid. For more fluid, a complicated venu-puncture can be necessary. Moreover, the sample preparation system must be low-cost since biological contamination concerns dictate that all material in contact with biological samples be discarded. It is also desirable that the sample preparation system be amenable to multiplexed operation.

BRIEF SUMMARY OF THE INVENTION

A sample preparation system that can fulfill the requirements for speed, cost, and performance described above is disclosed.

A porous material like a membrane filter can obviate the need for centrifugation or complicated micro-fluidic sample preparation. Since the membrane filters are compact and inexpensive, system cost is reduced, enabling stand-alone POC operation. Furthermore, the membranes can separate the plasma from the whole blood cells without additional support in under 30 seconds. Incubation of the filtrate with functionalized magnetic particles can achieve solution phase kinetics for rapid operation with sub pico-molar sensitivities. The use of an IC to perform the detection of the magnetic particles enables low cost, stand-alone operation. Therefore, the combination of a filter, capillary, magnetic particles and an IC can result in a stand-alone, accurate, multiplexed platform with the form factor of a thumb-drive. The size of the entire system excluding a battery and display can be reduced to under 1 cm3.

The assay system can be used for immuno-assays. The assay system can be used for nucleic acid, small molecule and inorganic molecule testing, or combinations thereof.

A sample preparation system comprising a membrane filter and a capillary channel configured to deliver magnetic particles to the exposed surface of an integrated circuit (IC) that manipulates and detects the particles is disclosed. The large particulate matter in the sample, such as whole blood cells, can be trapped on top or in the membrane, while the aqueous sample containing the target analytes traverses the membrane into the inlet of the capillary, where the magnetic particles can re-suspend and bind to the target analytes in the filtrate. The filtrate with the re-suspended magnetic particles can flow through the capillary and onto the sensing areas on the surface of the IC as a result of capillary action.

Magnetic particles bound to a target analyte can bind strongly through specific chemical interactions to the functionalized sensing areas on the surface of the IC. The number of magnetic particles specifically bound to the surface of the IC is representative of the concentration of the target analyte in the biological sample presented.

The surface of the IC can contain one or more sensing areas. The sensing areas correspond to the areas on the surface of the chip in which particle sensors can detect specifically bound particles. The particle sensors can be embedded in the IC. Particle sensors can be placed outside of the sensing areas to detect the non-specifically bound particles removed from the sensing areas for an accurate count of the total number of magnetic particles.

The IC can contain one or more magnetic force generators to manipulate the non-specifically bound magnetic particles on the sensing areas. These magnetic forces can be used to attract the magnetic beads to the sensing areas and to remove the non-specifically bound magnetic particles from the sensing areas. The system can have two or more capillaries, for example where the inlet of a delivery capillary is placed directly below the filter and delivers the filtrate into a sedimentation capillary which is placed vertically directly above the sensing area. The dried magnetic particles can be placed at the top of the sedimentation capillary. From the top of the sedimentary capillary, the dried magnetic particles can sediment to the sensing area once the filtrate reaches them. The length of time of the assay can be determined by the height of the sedimentation capillary.

The assay system may be configured to take whole or previously filtered blood, urine, tear, sputum, fecal, oral, nasal samples or other biological or non-biological aqueous samples.

Chemicals, such as, but not limited to: aptamers, oligonucloetides, proteins, agents to prevent clotting, target analytes for internal calibration curves, bindive catalytic agents, magnetic particles, or combinations thereof may be dried in the membrane filter assembly along the shaft of the capillary or on the surface of the IC and can be re-solubilized by the blood plasma but remain bound to the surface upon which they were dried.

The assay system can contain user interface controls to simplify user. The fully dry assay system can calibrate background signal and the native target signal. The assay system may invalidate the results if certain use-case conditions are not met.

The assay system may transmit the results to a secondary mobile device for storage and analysis.

BRIEF DESCRIPTION OF THE DRAWINGS

FIG. 2 is a cross sectional side view of a variation of the assay system 10 as the aqueous sample 5 is filtered and wicked via capillary action through a delivery capillary 14 into the surface capillary 15 and onto a surface 7 of the integrated circuit 12.

FIG. 3 is a cross sectional side view of a variation of the assay system 10 showing the aqueous sample 5 in the process of wicking up the sedimentation capillary 13 due to capillary action. Once the aqueous sample 5 reaches the top of the sedimentation capillary 13, the aqueous sample 5 can re-hydrate a reagent sphere 3, releasing the particles 4 to sediment onto the surface 7 of the IC 12.

FIGS. 4A and 4B are top and cross sectional side views, respectively, of a variation of the IC 12 containing a magnetic separation field generator implemented with separation conductors.

FIG. 5A is a cross sectional side view of cuvette 30 storing the dry sphere 3.

FIG. 5B is a cross sectional side view of cuvette 30 after the aqueous sample 5 dissolved the dried sphere 3 and released the particles 4.

FIG. 6 is a cross sectional side view of a cuvette with tapered side walls 40.

FIG. 7 is a cross sectional side view of a cuvette 30 with a cover 50 to contain the dried sphere 3 in the cuvette.

DETAILED DESCRIPTION

Biosensors that use non-magnetic or magnetic particle labeling to perform assays are disclosed. A particle can serve as an aid, or label, in detecting the presence or absence of a target analyte if the particle is attached to a chemical entity that reacts with the analyte, or analyte analogue, or analyte by-product. The reaction can be immunological, nucleic acid based, covalent, ionic, hydrogen bonding, van der Waals and other chemical reaction phenomena capable of promoting or inhibiting the labeled particle from binding to a surface.

Particles may be any spherical or arbitrarily shaped localized objects, from several nanometers to tens of microns in diameter, that modulate incoming light (e.g., reflect the light, refract the light, block or absorb the light, increase or decrease the intensity of the light, change the wavelength or spectral composition of the light). Particles may also be magnetic. Magnetic particles display diamagnetic, ferromagnetic, ferrimagnetic, paramagnetic, superparamagnetic, or antiferromagnetic behavior. Magnetic particles may include individual nanometer-sized particles of magnetic material (often referred to as magnetic nanoparticles or magnetizable nanoparticles) or larger aggregates of such magnetic nanoparticles to form an essentially spherical bead (often referred to as magnetic beads, magnetizable beads). Magnetic particles may be covered with or encapsulated by a non-magnetic material, such as a polymer, glass, ceramic, or any other non-magnetic material, that may be coated with biological or chemical molecules that react specifically to a target analyte. A non-magnetic material refers to any material that displays no magnetic properties or displays magnetic properties that are much smaller in magnitude (e.g., less than 0.001%) than the corresponding properties of the magnetic material in magnetic particles. Magnetic particles may be from several nanometers to tens of microns in diameter.

Figure 1:
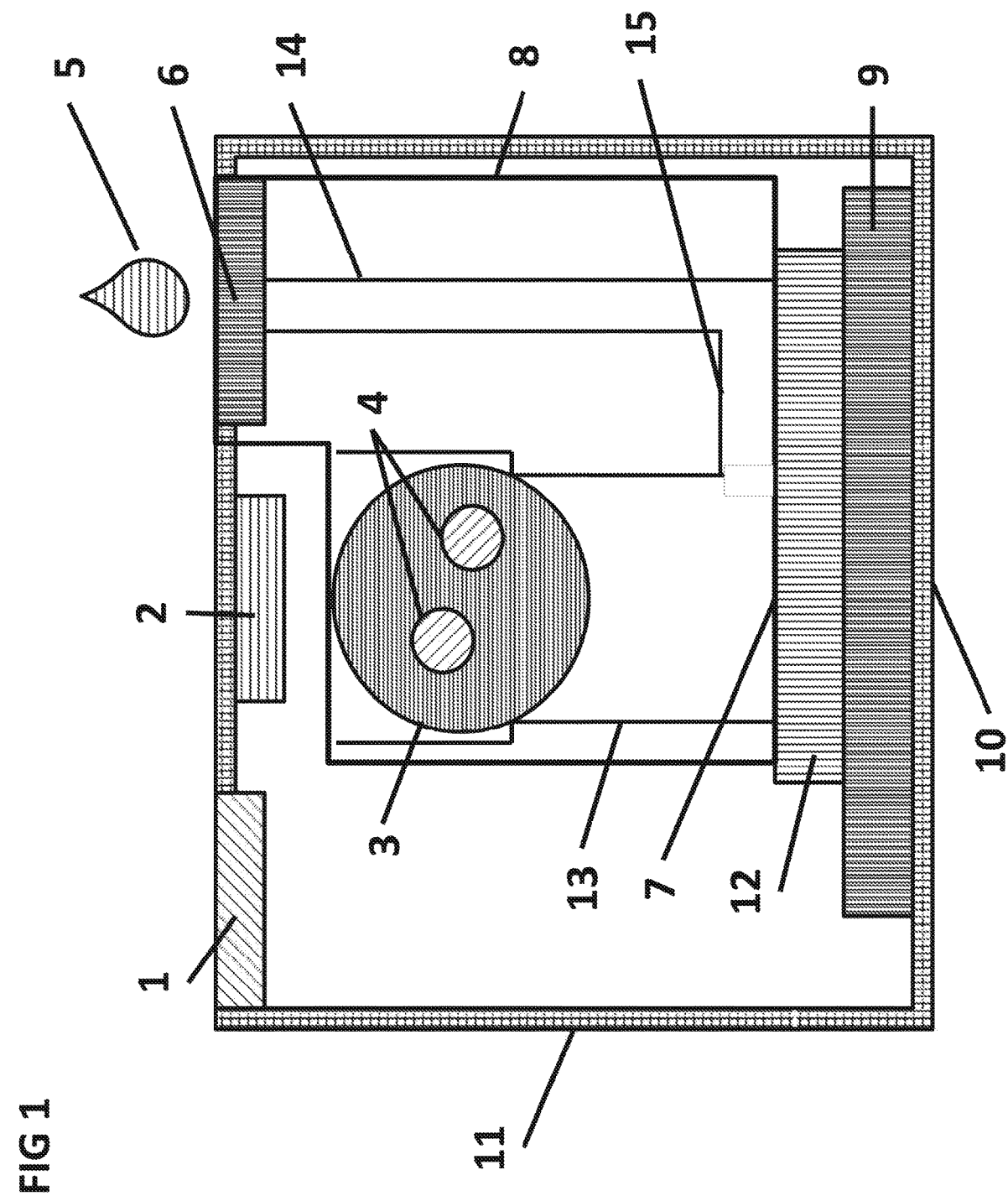
FIG. 1 is a cross sectional side view of a variation of the assay system 10 that includes a sample preparation and delivery module (SPDM) 8, a light source 2, an integrated circuit 12 (IC), a printed circuit board (PCB) 9, a display 1, and a casing 11.

FIG. 1 shows an assay system 10 that includes a sample preparation and delivery module (SPDM) 8, a light source 2, an integrated circuit (IC) 12, a printed circuit board (PCB) 9, a display 1, and a casing 11. The assay system 10 may be configured to perform a biological and/or chemical assay on an aqueous sample 5 by introducing, detecting, and/or quantifying particles 4 specifically binding on the surface 7 of the IC 12. An assay may be any procedure used to detect the presence of a target analyte or to quantify the concentration or amount of the target analyte in the aqueous sample 5. Target analytes may be enzymes, proteins, small molecules, nucleic acids, and other biological, chemical, and inorganic entities, or combinations thereof. The aqueous sample 5 may be whole blood, plasma, serum, diluted blood derivatives, spinal fluid, sputum, pulmonary lavage, fecal samples, oral samples, nasal samples, lachrymal fluid, other bodily fluids, laboratory samples, environmental samples, any other fluids potentially containing one or more target analytes, or combinations thereof.

Further, FIG. 1 shows a filter 6 that can be placed at the top of the SPDM 8. The filter 6 may be any type of filter (e.g., membrane filter, microfilter, syringe filter) capable of blocking or trapping particulate matter (e.g., red blood cells, white blood cells, other cells and micron to millimeter size particulates) and thus removing the particulate matter from the aqueous sample 5. The filter 6 may also be adapted to remove certain biological or chemical molecules from the aqueous sample 5 (e.g., a chemical coating on the filter 6 may remove molecules that compete with the target analyte or interfere, in any way, with the assay). Further, the filter 6 may include chemicals, molecules, and other dissolvable matter than may aid the assay protocol. For example, the filter 6 may contain dry anticoagulation factors that prevent blood samples from coagulating or dry assay additives to mitigate the effects of interferers in the sample. Further still, the filter 6 may be coated with hydrophilic material to aid in aqueous sample 5 absorption. The filter can be attached onto the top surface of the SPDM using double sided adhesive tape, transfer adhesive, hot melt adhesive, an epoxy seal along the edge, or by heat sealing or a similar bonding process. To minimize dead volume under the filter, the height of the double sided tape, transfer adhesive or epoxy seal can be less than 1 um, or less than 5 μm, or less than 10 μm, or less than 20 μm, or less than 50 μm or less than 100 μm, or less than 250 um.

Further, FIG. 1 shows a surface capillary 15, a delivery capillary 14 and a sedimentation capillary 13. The delivery capillary 14 can fluidically connect the membrane filter 6 to a surface capillary 15 allowing the aqueous sample 5 to flow from the filter to the surface 7 of the IC 12. The surface capillary 15 can fluidically connect the delivery capillary 14 to the sedimentation capillary 13 thus allowing the aqueous sample 5 to flow from the delivery capillary 14 into the sedimentation capillary 13 and up sedimentation capillary 13 to dry sphere 3. In one variation of the assay system 10, the filter 6 may be placed inside the delivery capillary 14 or surface capillary 15. The sedimentation capillary 13 may be placed vertically over the IC 12 and in contact with reagents containing particles 4. The reagents may be configured in a sphere (i.e., a reagent sphere 3) or any other shape. The reagent sphere 3 or other shape may rest on top of the sedimentation capillary 13 and may preferably be dry or lyophilized. The IC 12 may be mounted by any known method (e.g., wire-bonding, flip-chip assembly, conductive epoxy, and combination thereof) to a PCB 9. The assay system 10 can be encapsulated by a casing 11 with an opening for a digital display 1 and an opening for the filter 6. The display 1 may be driven by circuitry integrated on IC 12.

The SPDM 8 can be configured to accept an aqueous sample 5 from a sample source (e.g., a finger stick, a pipette, a syringe, a capillary tube, or combinations thereof), filter the aqueous sample 5 using the filter 6, deliver the filtered aqueous sample 5 first to the surface 7 of the IC 12 and subsequently to the reagent sphere 3, re-hydrate dried particles 4 within the SPDM 8, mix and incubate the particles 4 with the aqueous sample 5 and introduce the particles 4 onto the surface 7 of the IC. The systems and methods of use described herein can be applied to known SPDMs such as those described in PCT Application No. WO 2011/059512, filed 16 Nov. 2010 (titled: FILTRATION DEVICE FOR ASSAYS) and in PCT Application No. WO/2012/048288—

MAGNETIC PARTICLE BASED BIOSENSOR, which are incorporated by reference herein in their entirety. Other variations, components, and functions of the SPDM 8 are further described below.

FIG. 2 shows the aqueous sample 5 being wicked into the filter 6 where particulate matter such as whole blood cells can be blocked or discriminated by size. The aqueous sample can then be wicked from the outlet side of the filter 6 into the delivery capillary 14 and delivered into the surface capillary 15 and onto the surface 7 of the integrated circuit 12, as shown by an arrow. The flow of the aqueous sample 5 can continue from the surface 7 of the integrated circuit 12 up the sedimentation capillary 13 to the dry sphere 3. The flow in the delivery capillary 14, surface capillary 15 and the sedimentation capillary 13 can be maintained by capillary action. Once the capillaries are filled and the dry sphere 3 fully dissolved, the flow can cease. The amount of aqueous sample 5 in the SPDM can be precisely controlled by the inner volume of the capillaries to less than 0.5% variability, or to less than 1% variability or to less than 2% variability or to less than 5% variability. The inner volume of the capillaries can be used to precisely meter the amount of aqueous sample assayed. In cases where the assay system 10 is placed vertically as shown in FIG. 2 and the delivery capillary 14 and surface capillary 15 are below the filter 6, gravity can also assist the flow of the aqueous sample 5. Pressure from vacuum or pumping can also be used to facilitate the flow of the aqueous sample 5 through the delivery capillary 14 and surface capillary 15. As discussed above, the filter 6 may be a membrane filter and may have a surface area between 0.1 mm2 and 100 cm2 and a thickness between 1 µm and 10 mm. The membrane filter can be composed of polyvinylpyrrolidone/polyethersulfone (PVP/PES). The membrane filter can have a porosity gradient to effectively trap cells in whole blood while allowing blood plasma and the analytes therein to pass through the membrane. A preferable filter is a 0.26 mm thick PVP/PES filter with a 35 µm pore size on the top and a 2.5 µm pore size on the bottom. The membrane filter can be oriented in a horizontal plane. The membrane filter can be oriented in a plane parallel to the surface 7 of the IC 12. The delivery capillary 14 can be between 0.1 mm and 10 cm in length and between 10 µm and 5 mm wide. A preferable delivery capillary is 2 mm long and 0.25 mm wide. The surface capillary 15 can be between 0.1 mm and 10 cm in length and 10 µm and 5 mm wide. A preferable surface capillary 15 is 5 mm long and 0.5 mm wide. The magnetic particles may be dried on the bottom surface of the filter or inside the filter.

FIG. 3 shows the aqueous sample 5 in the process of wicking upwards inside the sedimentation capillary 13 due to capillary forces. Gravity can also assist the flow of the aqueous sample 5 up the sedimentation capillary 13 provided the sedimentation capillary 13 is placed below the bottom plane of the filter 6. Pressure from vacuum or pumping can also be used to facilitate the flow. Once the aqueous sample 5 reaches the top of the sedimentation capillary 13, the aqueous sample 5 can dissolve the dry reagent sphere 3 placed at the top of the sedimentation capillary 13. The particles 4 can be released and sediment through the aqueous sample 5 to the surface 7 of the integrated circuit 12, as shown by arrows. As the particles 4 sediment, the particles 4 can react with the target analytes in the aqueous sample 5 and bind specifically to the surface 7 of the IC 12. The sedimentation capillary 13 can be between 0.1 mm and 10 cm in length and 1 µm and 5 mm wide. A preferable sedimentation capillary 13 is 3 mm long and 1 mm diameter. The dry reagent sphere 3 can be manufactured by lyophilization and placed on the top of the sedimentation capillary 13 using an automated pick and place tool. Alternatively, the magnetic particles can be placed in a cuvette 30 by air flowing down the sedimentation capillary.

The surface 7 of the IC 12 can be illuminated by a light source 2. The light source 2 can generate and/or direct light to illuminate the surface 7 of the IC 12. The light source 2 may be or include a luminescent light source such as a light emitting diode (LED), laser emitting diode, incandescent light source such as a light bulb, any other source of light internal or external to the assay system 10, or combinations thereof. The light source 2 may be any external light source (e.g., the sun, an external lamp, ambient light in a room, and any other external light source that may be used instead of or in combination with an internal light source to illuminate the surface 7 of the IC). The light source 2 may be positioned anywhere in the assay system 10 or external light may be inputted anywhere into the assay system 10 and an optical module may direct the light onto the surface 7 of the IC 12. The light source 2 may be integrated on the IC 12 itself. For example, a direct semiconductor may be used to fabricate light 2 in the IC 12 or a portion of a direct semiconductor may be added to the IC 12 (e.g., via wafer bonding, molecular beam epitaxy, and other suitable fabrication processes). The light source 2 may be configured to produce a light intensity anywhere from 1 mW/m2 to kW/m2. The light source can be powered by a battery to eliminate the AC tones prevalent with distributed power sources. The light source can illuminate more than one sensing areas on one IC or more than one sensing area on more than one ICs. The activation of the light source and control of its intensity can be done by circuitry embedded in the IC 12.

A shadow may refer to any type of light modulation caused by a particle 4 in the direction of propagation of light that increases or decreases intensity, changes the spectral composition, blocks, changes the polarization, or otherwise modifies the properties of said light. One or more light sources can be situated or positioned directly above the integrated circuit 12 such that particles 4 situated above the surface 7 of the IC 12 cast a shadow that is projected downward onto the surface 7 of the IC. The shadow then may be detected by one or more optical sensors 40 situated below the surface 7 of the IC 12. However, the light source(s) may be positioned and directed at any angle relative to the surface 7 of the integrated circuit 12 such that the light shines on least a portion of IC 12 surface 7. Light at or near the red spectrum (550-750 nm) may offer superior SNR since human whole blood and plasma samples have an absorption minimum at that frequency.

In a variation of the assay system 10, multiple sources of light may illuminate the surface 7 of the IC 12 indirectly and/or at oblique angles. Multiple ICs can be illuminated by one source of light or multiple sensing areas on the same IC can be illuminated by one light source. Alternatively, one or more sensor regions on one or more ICs can be illuminated by more than one light source. The shadows or otherwise the modulated light due to the particles 4 can be projected at oblique angles (i.e., not straight downward).

One or more reflectors, one or more lenses, one or more optical fibers, one or more light pipes, and any other component or combination of components may be used to direct light onto the surface 7 of the IC 12. The light source 2 may be positioned on or integrated into the PCB 9 and a reflector placed on the ceiling of the casing 11 above the IC 12, or an optical fiber or light pipe may direct the light originating from the light source 2 onto the surface 7 of the IC 12. The light source 2 may be modulated (e.g. turned on and turned off repeatedly) at a certain frequency, at multiple frequencies, following a certain predetermined or random sequence in time, or combinations thereof. For example, the light source 2 may be turned on for a predetermined amount of time prior to introducing the particles 4 in order to calibrate the optical sensors 20 on the IC 12 (e.g., by measuring the sensitivity, sensitivity distribution, saturation level, and other relevant parameters of the optical sensors 20 and underlying electronic circuits) and to calibrate the light source 2 (e.g., measure and adjust the light intensity, light uniformity, and other relevant parameters of the light source 2). Subsequently, the light source 2 may be turned on for a predetermined amount of time to allow for a shadow or any other form of light modulation to be created by the particles 4 and detected by the optical sensors 20.

The SPDM 8 can be opaque such that light from the light source 2 can only be transmitted through the sedimentation capillary 13. Multiple sedimentation capillaries above one or more ICs can allow the propagation of light from one or more light sources to one or more sensor regions. The SPDM can be partially opaque or portions of the SPDM can be opaque to optimize the quality of the light transmitted onto the surface of the chip. The SPDM can be composed of two discrete portions, one opaque and one translucent or transparent. The transparent region of the SPDM 8 useful when there is opaque material in the sedimentation capillary 13, like the dry sphere or lysed aqueous sample, that need to be circumvented by the light in order to illuminate the particles 4 on the surface 7 of the IC 12. For example, in the SPDM a thickness along all or part of the length of the sedimentation capillary 13 can be transparent to allow the light to reach the surface 7 of the IC 12, while the rest of the SPDM 8 can be opaque. For example, the top portion of the SPDM 8 containing the cuvette 30 and to top of the sedimentation capillary 13 can be transparent, while the bottom portion of the SPDM 8 containing the rest of the sedimentation capillary can be opaque. The SPDM can be created by laminating, gluing, or otherwise binding two layers of material, one opaque and one transparent or translucent. The transmission of the light onto the surface of the chip can also be used to determine if aqueous sample 5 has reached the top of the sedimentation capillary in the SPDM and whether the dry sphere 3 has dissolved. Light pipes or optical fibers and capillaries 13, 14 and 15 can be combined in a single unit made of plastic (PMMA, PDMS or other silicon derivatives, polycarbonate, polyacetate, polyurethanes, polyvinylchloride, or other synthetic polymers).

Image processing filters can be used to eliminate illumination artefacts for superior particle detection signal to noise ratio. The image processing filter algorithm can be hard-coded onto the IC 12, embedded in the memory on the IC 12 or described in software stored on the IC 12 or on an external IC. Examples of the image processing filters include spatial low pass filters, un-sharp masks, convolution matrices and other algorithms that combine the raw optical signals from multiple sensors in a logical algorithm to reduce or eliminate the components of the raw optical signals that are detrimental to particle shadow detection signal to noise ratio. In this way, the image processing filter can be used for example to estimate the background illumination, cross-talk between adjacent or nearby optical sensors, global shadows, bead aggregates and reflections on the surface 7 of the IC 12 due to constructive and destructive optical interferences. The image processing filter can eliminate or reduce the shadows resulting from debris or other blemishes on the surface 7 of the IC 12 that does not correspond to a magnetic particle.

To minimize stray light from the environment or external light sources, the sample port where the sample is applied on the device, for example the filter opening, can have an opaque lid that closes after application of the sample. The opaque lid can be limited to covering only the sample port or can large enough to cover the entire device. The opaque lid can be hinged, screwed, clipped or fastened on.

Illumination information from the optical sensors can be interpreted by the IC 12, which can generate the commands to direct the one or more light sources to alter the illumination characteristics. The intensity, the color, the incident angle, the position, the coherence and the number of light sources and their constellation can all be directed according to the illumination information from the optical sensors in order to improve detection signal to noise ratio.

Multiple light sources producing illuminations of different color can be used to identify magnetic particles of different color. A first light source 200 can produce an illumination of a first color 201 and a second light source 210 can produce an illumination of a second color 211 onto the surface 7 of the IC 12. A first particle 202 can be dyed or colored with color 201 and a second particle 212 can be dyed or colored with color 211. Particles 202 and 212 can bind specifically atop optical sensors embedded in the IC 12. For equivalent illumination intensities from light source 200 and light source 210, the intensity of the shadow cast by particle 202 on the optical sensor resulting from the illumination of light source 200 will be different from the intensity of the shadow cast by particle 202 on the optical sensor resulting from the illumination of light source 210. Similarly, for equivalent illumination intensities from light source 200 and light source 210, the intensity of the shadow cast by particle 212 on the optical sensor resulting from the illumination of light source 200 will be different from the intensity of the shadow cast by particle 212 on the optical sensor resulting from the illumination of light source 210. The color of a particle can be determined by measuring the relative intensities of the shadows resulting from light sources of different color. The lights of different color can be turned on sequentially or at the same time. The optical sensors can identify the color of a colored particle by measuring one or more frequencies of the absorbance, reflectance, transmittance phosphorescence, or fluorescence spectrum of the shadow cast by a colored particle. The color of the shadow is the complementary of the particle. More than one light source of more than one color can be used to illuminate the colored particle with more than one wavelength of light, thereby providing a spectral signature of the colored particle. A broad spectrum light can be used for calibration. Various intensities can be used for various illumination colors and the relative intensities of the shadow, or absorbance, reflectance, luminescence, fluorescence, phosphorescence or transmitance of the colored beads can be used to identify the color of the bead. Mono-chromatic, or multi-chromatic lights can be used. Coherent, collimated or diffuse lights can be used. Optical sensors sensitive to different detection spectrums can detect the shadows from colored particles and thereby can identify the color of the particle. A single optical sensor that can measure illumination intensities at different optical frequencies can be used to determine the color of a particle casting a shadow on it.

Multiple optical sensors sensitive to different optical spectra can be used to determine the color of a particle. The cross sectional area of the optical sensors can be smaller than the cross sectional area of the shadow of the colored particle so that they can be laid out to measure the intensity of the shadow from the same particle.

Optical sensors that are sensitive to different optical spectra can be activated to detect the same shadow at the same time, or they can be activated to detect the same shadow in an alternating sequence.

Particles of the same color can be coated with one or more reagents that react specifically to one or more targets such as epitopes or one or more chemical groups or moieties on the same target. Particles of different color can be coated with different reagents that react specifically to different targets. Particles 202 can be coated with a first antibody 222 and particles 212 can be coated with a second antibody 232. Particles 202 and 212 can be dried in the same dry sphere 3 or can be dried in separate dried spheres. Particle 202 and 212 can sediment in the same sedimentation capillary 13 or sediment in separate sedimentation capillaries. The surface of the chip can be coated with chemical reagents that bind specifically in a capture format to particle 202 in the presence of a first specific target 242. The surface of the chip can be coated with chemical reagents that bind specifically in a capture format to particle 212 in the presence of a second specific target 243. Particles of different colors can be selectively identified and the concentration of their targets measured at the same time or in sequence. Multiplexed assays can be performed simultaneously on the same chip. The number of particles of the same color can range from 1 to 100.000 to 1 trillion. The number of different colors can range from 1 to 1000. Each target can have a unique color, or multiple targets can share one color or one color can identify multiple targets.

Examples of multiplexed embodiments:
1—entire chip is coated with a mixture of antibodies and all particles of the same color are derivatized with a specific antibody;
2—specific sites of the chip are derivatized with 1 specific antibody. Using specific colored particles (such as beads) per assay allows determination of cross-reactive binding when wrong color beads is at the wrong location;
3—when a certain bead is derivatized with multiple antibodies, multiplexing is preferably achieved by derivatizing specific locations of the chip with specific antibodies.

The IC 12 can be a substrate that can incorporate one or more optical sensors 20 and associated electronic circuits. At least a portion of the surface 7 of the IC 12 is coated with reactive molecules and the IC 12 is configured to accept particles 4 that may bind specifically (i.e., via the reactive molecules) or non-specifically to the surface 7 of the IC 12, depending on the concentration of the target analyte. The IC 12 may be used to remove from atop the sensors any non-specifically bound particles and quantify the number or concentration of remaining specifically bound particles. The number of specifically bound particles may be proportional to the concentration of the target analyte in the sample. Generally speaking, specifically bound particles are particles that are bound to a surface 7 via at least one specific binding interaction (i.e., antibody-antigen binding). Generally speaking, non-specifically bound particles are particles that are bound to the surface 7 with weaker binding forces (e.g., van der Waals forces). Specifically bound particles refer to particles that are bound with one or more specific biochemical interactions such as one or more antigen-antibody binding interactions and other interactions discussed above and are not removed from the surface 7 by on-chip generated magnetic separation forces. Non-specifically bound particles may be particles that are removed from the sensing area 21 by on-chip generated magnetic separation forces. Non-specifically bound particles may still contain one or more specific binding interactions but generally contain fewer specific binding interactions than specifically bound magnetic particles. For example, for large particles (e.g., those greater than 100 nanometers in diameter), multiple specific binding interactions may be required for the particles to remain stationary in the presence of separation forces (i.e., to be considered specifically-bound). For example, particles with 2 or more antigen-antibody binding interactions may be never removed with separation forces and thus are always considered specifically bound, particles with fewer than one antigen-antibody binding interactions may be always removed with separation forces and thus are considered non-specifically bound, whereas particles in between may be either specifically-bound or non-specifically bound. The magnetic separation forces can be tailored to select the desired number of antigen-antibody interactions necessary to keep a magnetic particle specifically bound to the surface. In so doing, the number of magnetic particles remaining specifically bound to the surface can also give an indication of the total number of antigen-antibody interactions attaching the particles to the surface 7 of the IC 9.

The bio-chemical functionalization and the magnetic forces can be tailored to ensure that only 1 specific molecular interaction (such as one antigen-antibody interaction, one strand of DNA, a complementary strand of DNA, a covalent bond, a hydrogen bond, is sufficient to specifically bind a magnetic particle to the surface 7 of the IC 12. Magnetic particles larger than 100 nm, such as between 100 nm and 1 um, or between 1 um and 10 um, can also be configured in the system to bind specifically to the surface 7 of the IC 12 through one single specific molecular interaction. The on-chip generated magnetic separation forces can be tailored to pull away from the sensors the magnetic particles that have no specific molecular interactions to the surface. The on-chip generated magnetic separation forces can be tailored to leave immobilized the magnetic particles that have exactly one specific molecular interaction to the surface. A magnetic particle sensor can detect a single magnetic particle and by extension, a magnetic particle sensor can be used to detect a single specific molecular interaction between the surface 7 of the IC 12 and a magnetic particle. An array of individually addressable magnetic particle sensors can be used to detect multiple magnetic particles specifically bound to the surface 7 of the IC 12 through single specific molecular interaction. The array of magnetic particle sensors can be used to count the number of specific molecular interactions in the sensing area on the surface 7 of the IC 12.

The assay system 10 can be handheld and portable. It can be less than 1 L, 0.1 L, 0.01 L, or 1 mL in volume and weigh less than 1 kg, 100 g, 10 g or 1 g.

Particles may serve as light concentrators through internal or external reflections. For example, the amount of light incident on optical sensors 20 may be increased by over 1% and optical sensors on the IC can be configured to detect this light intensity increase. The particles may modulate the light (e.g., filter the frequency spectrum of the light, luminesce with another frequency of light, change the color or polarization of the light, fluoresce, or phosphoresce). Likewise, the optical sensors 20 may be configured to detect any of these color or polarization changes, for example by using color or polarization filter arrays placed over the optical sensors 20 or by using different optical sensor 20 types such as N-well diodes, N+ diodes, poly gate diodes, and P+ diodes, which are sensitive to different optical spectra or frequencies. The electronic circuits may be any combination of metal or semiconductor connections, resistors, capacitors, inductors, transistors, diodes, amplifiers, digitizers, digital logic, and other integrated electronic circuits used to obtain, forward, process, and output a signal from the optical sensors 20. The circuitry may be used to individually address any of the optical sensors 20 in an array, either sequentially or in parallel. The IC may be fabricated in any commercial integrated circuit process (e.g., CMOS, CCD, BJT) or may be made in a custom fabrication process. Other variations, components, and functions of the IC 12 are further described below. Optical sensors 20 can distinguish between different color beads by the relative amount of light they transmit from the different color light sources. Optical sensors 20 can distinguish different wavelengths of light that are emitted by different particles such as beads.

The PCB 9 can be any rigid or flexible substrate that stores the IC 12 and electrically and/or mechanically connects the IC 12 to any other components. The PCB 9 can contain one or more batteries, one or more control modules, one or more voltage regulators, one or more sensors, one or more actuators, one or more displays, and combinations thereof. As discussed above, the PCB 9 may also include the light source 2 that can provide light into the IC 12 via an optical module. The PCB 9 may be placed on the bottom of the housing or in any other position in the housing and may contain connectors and daughter-boards or any other extensions that may contain any of the components described above or described below in any position and orientation inside or outside the housing containing the SPDM 8. The PCB 9 components internal to the assay system 10 and the circuitry and sensors of the IC 12 may be controlled by a control module integrated on the IC 12 (e.g., a control module core, a discrete control module mounted on the PCB 9, a central processing unit (CPU), a digital signal processing (DSP) unit, a field-programmable gate array (FPGA), or any other control module or combination of control modules. The terms control module core and control module may be used interchangeably in this specification and may be located on the PCB 9, in the IC, or in any other part of the assay system 10. The control module may store assay calibration parameters and assay protocol algorithms. Assay calibration parameters may include a standard curve that relates the number or concentration of particles 4 detected to the concentration and/or amount of the target analyte in the aqueous sample 5. Assay calibration parameters may also include an assay time which may include any time intervals between different steps in an assay (e.g., time from aqueous sample 5 detection to optical sensor array readout, readout duration, magnetic separation force duration, magnetic separation intervals and any other time interval). Assay calibration parameters may also include magnetic separation force and magnetic concentration force strength, duration, frequency, pattern. Assay calibration parameters may include any other parameters that may affect assay results. The assay calibration parameters are adjusted in response to measurements made by any sensors and components of the assay system 10. The battery or the battery unit can be removed in an easy pop-out system or otherwise separated prior to discarding the system. Portions of the circuitry or the entire electronic module including display can be popped out or separated from the rest of the device prior to discarding the system.

The assay system 10 can contain one or more inertial sensors. The inertial sensors may include accelerometers, gyroscopes, tilt sensors, and any other sensors capable of detecting and quantifying position, velocity, acceleration, orientation, and combinations thereof. The inertial sensors are configured to sense the physical parameters discussed above and output them to the control module. The control module may be configured to read the output from the inertial sensors and determine if any of the physical parameters are unusual and/or out of the acceptable range. For example, the inertial sensors may send an output to the control module indicating that the orientation of the assay system 10 is incorrect (e.g., the IC 12 is at on a tilt for a prolonged period of time) or the acceleration of the assay system 10 is too high (e.g., a user is moving the assay system 10 beyond the recommended limits while the magnetic separation is being performed). As a result, the control module may send a signal to the user via the display 1 that an incorrect action took place and that the results of the assay are invalid. The control module may send a signal to the user via the display 1 that an incorrect action took place and that the position of the device must be adjusted in order for the assay to proceed normally. Alternatively, the control module may attempt to compensate for any effects resulting from incorrect orientation and/or applied acceleration. The control module can modify and/or selects the assay calibration parameters based on the measured values of relevant physical parameters. The control module can perform more detailed compensation on the sensor level, for example, by applying different weights to signals from different optical sensors 20 positioned in different locations on the IC, or completely ignoring the reading from certain optical sensors 20 altogether. The control module may also modify the assay time based on the reading obtained from the inertial sensors (e.g., the optical detection may be turned on sooner/later, allowing particles 4 less/more time to incubate with the target analyte, respectively). The inertial sensors may be mounted in any component of the assay system 10 (e.g., mounted as a chip on the PCB 9, integrated into the IC, mounted on any wall of the casing 11, or combinations thereof).

The optical sensors and other sensors can be used to validate the manufacturing of the assay system 10. The assay can be invalidated if too many or too few magnetic particles are detected on the surface 7 of the IC 12. Too few magnetic particles can be an indication of the assay system 10 being tilted during use, while too many particles may be an indication of a manufacturing process problem. The assay can also be invalidate the assay if the surface density of the magnetic particles detected is not approximately uniform. This can also be an indication that the assay system 10 was tilted during use. The assay system 10 can also detect aqueous leaks in the double-sided tape by monitoring whether the magnetic particles move across the surface 7 of the IC 12 when no strong magnetic forces are applied.

The PCB 9 and/or the IC 12 may contain a read-only memory module (ROM), a random access memory module (e.g., SRAM, DRAM), or other module capable of storing data (PROM, EPROM, EEPROM, Flash, and any other storage medium). The data module may be part of the control module and may be used to store calibration data from the various sensors, actuators, and modules in the assay system 10 that is derived just prior, during, or after performing an assay. The data module may store calibration data generated during the design process or after the IC 12 is manufactured and/or the assay system 10 is assembled. For example, the calibration data may compensate for variations in manufacturing (e.g., ILD thickness, optical sensor 40 sensitivity, and other parameters that may vary during manufacturing). In another example, the calibration data may compensate for variations in surface coating (e.g., surface chemistry, reactive molecule density, reactive molecule type, and other parameters that can vary during surface 7 coating). The calibration data can include assay calibration parameters that are derived from one or more chips in a particular batch (e.g., from the same wafer, same surface coating batch, same assembly batch).

The assay system 10 can include one or more temperature sensors. The temperature sensors may include a thermistor, a semiconductor sensor, a thermocouple, a temperature-dependent resistor, or combinations thereof, and may be configured to measure the temperature of the surroundings (e.g., the air temperature outside the assay system 10, the temperature of the SPDM 8, and/or the temperature in the vicinity of the IC 12) or the temperature of the aqueous sample 5 directly (e.g., the SPDM 8 may be configured to place the temperature sensor in contact with the aqueous sample 5, or the sensor may be located at or near the surface 7 of the IC 12). An assay may have distinct assay calibration parameters (e.g., standard curve, assay time) at each temperature level and as the assay kinetics may be sped up or slowed down depending on the temperature level. Accordingly, the temperature reading may be sent to the control module and may be used to adjust the assay calibration parameters to compensate for the changes in temperature. Aside from being integrated or attached to the PCB 9, the temperature sensor may be mounted in any other component of the assay system 10 (e.g., integrated into the IC 12, mounted on any wall of the casing 11, or combinations thereof). The IC 12 or SPDM 8 may contain one or more heating elements (e.g., resistors, coils, wires) that can be used to keep the temperature of the surface 7 of the IC 12, the aqueous sample 5, and/or the entire assay system 10 at a nearly constant, predetermined value. The information from the temperature sensors can be read and the control module can control the heating elements in order to keep the temperature constant in the range of 20° C. to 40° C.

The assay system 10 can include one or more moisture sensors. The moisture sensor(s) may be placed in contact with the aqueous sample 5 and may be used to detect the presence of the aqueous sample 5 (e.g., using electrodes to detect a change in resistance or a change in capacitance between the electrodes as a result of the presence of the aqueous sample 5). The moisture sensor(s) may send a signal to the control module, either continuously or upon detection of the aqueous sample 5, indicating the moisture level reading, and the control module may enable other components of the assay system 10 upon receiving a signal indicating the presence of the aqueous sample 5. Aside from being integrated or attached to the PCB 9, the moisture sensor may be mounted in any other component of the assay system 10 (e.g., integrated into the IC 12, mounted on any wall of the casing 11, or combinations thereof).

The PCB 9 can include one or more viscosity sensors. A viscosity sensor can be placed in contact with the aqueous sample 5. The viscosity of blood plasma can vary. Higher fluid viscosities may lead to longer assay kinetics and longer particle sedimentation times. Accordingly, the viscosity sensor(s) may send a measurement of the viscosity to the control module which in turn may modify the assay time and other assay calibration parameters. Aside from being integrated or attached to the PCB 9, the viscosity sensor(s) may be mounted in any other component of the assay system 10 (e.g., integrated into the IC 12, mounted on any wall of the casing 11, or combinations thereof). By including temperature, viscosity, orientation, acceleration, and any other environmental factors into account when performing an assay, the results of the assay may be adjusted appropriately, via the assay calibration parameters, to effectively cancel out these environmental effects, leading to increased robustness, accuracy, and consistency of results in diverse environments and settings. The moisture sensors placed at different points along the path of the aqueous sample 5 can be used to measure the viscosity of the fluid. Alternatively or in combination, the optical sensors 20 can be used to measure the time from the reagent sphere 3 dissolution to the time the particles 4 sediment onto the surface 7 of the IC 12. This time can also be used to determine the viscosity and incubation time information.

The assay system 10 can include a vibrator module. The vibrator module may include an electric or piezoelectric motor with an unbalanced mass, a piezoelectric or electromagnetic acoustic or ultrasonic transducer, or any other module and method for generating vibrations. The vibrator module may be turned on during the sample delivery steps (i.e., between the time when the aqueous sample 5 is introduced and the time the particles 4 finish sedimenting on the surface 7 of the IC 12) in order to agitate the aqueous sample 5 and/or the particles 4 and allow the particles 4 to more quickly disperse in the aqueous sample and speed up assay kinetics. The vibrator module may be enabled upon detection of the aqueous sample 5 when the aqueous sample 5 comes in contact with the SPDM 8 and/or the IC. The amplitude, frequency, and/or pattern of the vibrations can be controlled by the control module and adjusted based on various parameters obtained from the environmental sensors discussed above and based on any assay calibration parameters. For example, vibration amplitude may be increased if the temperature is low and/or the viscosity of the aqueous sample 5 is high in order to speed up assay kinetics.

A capacitive, inductive or resistive humidity sensor can be used to detect the presence of the aqueous sample 5 on the surface of the IC 12. The humidity sensor can be embedded in the IC 12 under the sedimentation capillary 13 or under the surface capillary, or under the delivery capillary.

The PCB 9 can contain one or more external electromagnets or permanent magnets generating fields from 0.1 µT to 1 T at excitation frequencies from DC to 100 MHz. Magnets can have an appreciable effect on the particles 4 if the particles 4 are magnetic particles. A permanent magnet may be placed below the IC 12 or in close proximity to the IC 12 in order to pull magnetic particles more quickly towards the surface 7 of the IC 12 (i.e., increase the sedimentation velocity of the magnetic particles to as high as 10 mm per second). The permanent magnet may be replaced with an electromagnet (e.g., Helmholtz coil, current line, or combinations thereof) mounted onto the PCB 9 and below the IC 12 to selectively generate magnetic fields and magnetic forces. A second electromagnet may be placed above the IC 12, near the ceiling of the casing 11, in order to pull the magnetic particles up from the sensor surface 7. This could be used to increase the incubation time to over 10 minutes or to perform magnetic separation steps. One or more electromagnets may be placed on the sides of the PCB 9 around the sedimentation capillary or extend into the assay system 10 and around the sample chamber in order to generate lateral forces on the magnetic particles. Any of the electromagnets placed above, below, or to the sides of the sample chamber may be used to agitate the magnetic particles (e.g., move them side to side, make them vibrate, make them change orientation) in order to create convective forces in the aqueous sample 5 and/or to more quickly sediment the magnetic particles to the IC 12 surface 7. Electromagnets configured to generate lateral forces may be used to compensate for any tilt in the assay system 10 (e.g., if the assay system 10 is tilted to the left, an electromagnet on the right side may turn on to ensure magnetic particles sediment evenly and do not aggregate on the left side of the IC). The permanent magnets or electromagnets may be mounted in any other component of the assay system 10 (e.g., integrated into the IC, mounted on any wall of the casing 11, or combinations thereof).

The assay system 10 can be run with the IC 12 at the top and with its surface 7 facing down. A permanent or electromagnet can be placed above the IC 12 to pull the magnetic particles 4 upward to its surface. In this way, the system can run without the filter directly on whole blood since the red blood cells will settle downwards, away from the surface of the IC. Alternatively, the system can be run directly with lysed samples. The whole blood filter can be replaced by or stacked with a hydraulically permeable solid membrane or matrix to ensure even and efficient mixing of the cellular material with a lysing agent and other dry reagents.

The display 1 can be any display known in the prior art (e.g., LCD display. LED display, OLED display and any other type of display, touch-screen) that may display the presentable assay information generated or stored by the chip 12 (e.g., concentration of one or more target analytes, amount of one or more target analytes, coefficient of variance, timestamp, timing of the assay, validity of the results, patient and device identification number, temperature, humidity, internet/telephone/physical locations, help/counselling and information, angular information of the device, device ID, patient ID and any other relevant results). The presentable assay information may include status indicators that can signal the device is ready, busy, testing, done, or in an error state. The presentable assay information can include error messages that indicate the device is tilted, additional sample is needed, the on-board controls failed to fall within expected range, temperature or humidity over/under the specified range or an expiration date has been exceeded. The presentable assay information may include information on the sample (e.g. whether it is lysed, the viscosity, turbidity, lipemia, color of sample). The presentable assay information may include written or visual instructions to the user on how to use the assay system 10 to perform a measurement. A speaker or earphone jack may also be integrated into the assay system 10 to deliver the presentable assay information in an audio format.

The presentable assay information can be displayed in an encrypted format alone or alongside the presentable assay information in a non-encrypted format. The display 1 can also display a portion or all of the presentable assay information as a one dimensional bar code or dimensional QR code or other machine-readable format. The results can appear as an encrypted hexadecimal code or using other symbols or shapes. Users can take one or more still photographs or one or more videos of the display 1 using a secondary mobile device to retrieve and decrypt a portion or all of the presentable assay information. The user can have a medical software application installed on a secondary mobile device that processes the photograph or video of the display to retrieve and decrypt the presentable assay information. The medical software application can prompt the secondary mobile device's user for a patient ID or can retrieve directly from the secondary mobile device's login information. The presentable assay information retrieved by taking the photograph or video of the display can be bound to the patient ID in a secure manner, for example in a HIPAA compliant manner. The display can be deactivated or the presentable assay information can be removed from the display after a pre-set time, or once a user presses a button or the a touch-screen integrated into assay system 10 or from a prompt from the medical software application. Telecommunication by taking still photographs or videos of the display 1 does not require any additional hardware either on the assay system 10 or on the secondary mobile device and is therefore universally interoperable with all modern consumer smart devices.

The medical software application can also store the presentable assay information on the secondary mobile device and can graph the presentable assay information. The medical software application can combine the presentable assay information with historical medical information from the patient. The medical software application can connect the secondary mobile device wirelessly or through a wire to a third storage device for processing and storing the presentable assay information. The medical software application can store or transmit all or portions of the presentable assay information to a third device.

Presentable assay information can be transmitted to and stored on the secondary mobile device without being displayed on display 1. The medical software application can prompt the user to get in contact with a doctor, counselor, insurance company representative, drug company representative, clinical trial representative, a reporting agency or other third party in order to gain access to the presentable assay information. The medical software application can automatically contact a third party and direct transmission of all or part of the presentable assay information to that third party. Example includes the CDC or other healthcare professionals in the cases where public safety is at risk. The medical software may omit the patient ID when sending information third parties, but can include information like the time and location of secondary wireless device. The medical software application can combine the presentable assay information with other information found on the secondary wireless device, such as time of day, location, login information, contact to healthcare professionals, emergency contacts, age and sex of patient or other patient information stored on the secondary mobile device The medical software application can be stored on the chip 12 or in other storage devices integrated in assay system 10 and transmitted to the secondary mobile device prior to performing the assay, after running the assay or during the assay. The web location and/or routing information of the medical software application can be stored on the chip 12 or in other storage devices integrated in assay system 10 and can be included in the presentable assay information. The assay system 10 can prompt the secondary mobile device to download the medical software application by transmitting the web location or routing information.

The device can also provide multiple different sets of results. A first set of displayed results can be displayed and provided to the user and a second for example more detailed set of comprehensive results can be sent to a third party.

A patient or user untrained as a caregiver, such as a family member or home health aide can perform the assay without help from trained healthcare professionals. For special applications like drug monitoring or emotionally difficult applications like HIV testing, it may be undesirable for the patient to examine all or part of the presentable assay information prior to their examination by a third party. The device can encrypt and transmit some or all the presentable assay information to a third party for review without displaying them or granting access to them to the patient. The third party can review the presentable assay information and re-transmit reviewed assay information back to the patient, or re-transmit access to the presentable assay information, or re-transmit a different set of information or additional information. The patient or user may be required by the device to send the presentable assay information the secondary mobile device to a third party in order to receive the reviewed assay information or access to the latter. The presentable assay information can be encrypted in a way that can only be decrypted by the third party. The patient may or may not be the user of the secondary mobile device or the assay system 10. A healthcare professional, a family member or an untrained home health aide may or may not be the user of the secondary mobile device or the assay system 10. The secondary mobile device can be a tablet, a phone or any wireless telecommunication device.

Presentable assay information and the medical software application can be relayed to the secondary mobile device wirelessly by assay system 10 (for example using Bluetooth, Zigbee or Wifi protocols), visually on the screen, capacitively using parallel plate, inductively or via optical links such as IR communication or taking still photographs of the display 1. The assay system 10 can contain full duplex communication with a transceiver device. The assay system 10 can have an optical link or a bar code reader integrated into it. The transceiver device can send to the assay system 10 information regarding which assays were ordered, and additional patient information like sex or age of patient or other pertinent information to the assay. The assay system 10 can modify the assay according to the received information. In a multiplexed format, some assay may not be run, or may be run but not reported if they weren't ordered.

The casing 11 can be an external shell that houses all the other components of the assay system 10. The casing 11 may be made in any standard or custom manufacturing process (e.g., injection molding) and may be made from any standard material (e.g., plastic). The casing 11 may also include an outer flap over the sample inlet or over the entire device to reduce the amount of light that can shine through the seams of the casing 11.

The IC 12 can include one or more optical sensors 20 configured in an array. Each optical sensor 20 may be integrated into the IC 12 and implemented in any technology (e.g., junction photodiodes, avalanche photodiodes, PIN photodiodes, active pixel sensors, charge-coupled devices, light-sensitive resistors, or other solid-state optical sensors 40). Each optical sensor 20 may be individually addressable and may output electrical signals that may be amplified, digitized, stored and processed by circuitry on the IC 12 and/or the PCB 9. Each optical sensor may be configured to detect a shadow cast by a particle as a result of the particle blocking the light rays from the light source. For example, an optical sensor can detect a particle because the particle casts a shadow over the sensor, decreasing the light intensity incident on optical sensor from the light source. Consequently, as a result of a particle blocking a portion of the light from the light source, optical sensor generates a signal that is different from a baseline signal without the particle, thus indicating the presence of a particle over the sensor.

Magnetic particles in the sensing area 21 on the surface 7 of the IC 12 can be detected by magnetic sensors integrated in the IC 12 as in WO/2009/091926—INTEGRATED MAGNETIC FIELD GENERATION AND DETECTION PLATFORM, reference here in its entirety. Hall sensor, GMR sensors. AMR sensors, variable inductance current lines can all be used as magnetic sensors. If magnetic sensors are employed, the light source 2 can be omitted.

Figure 4B:
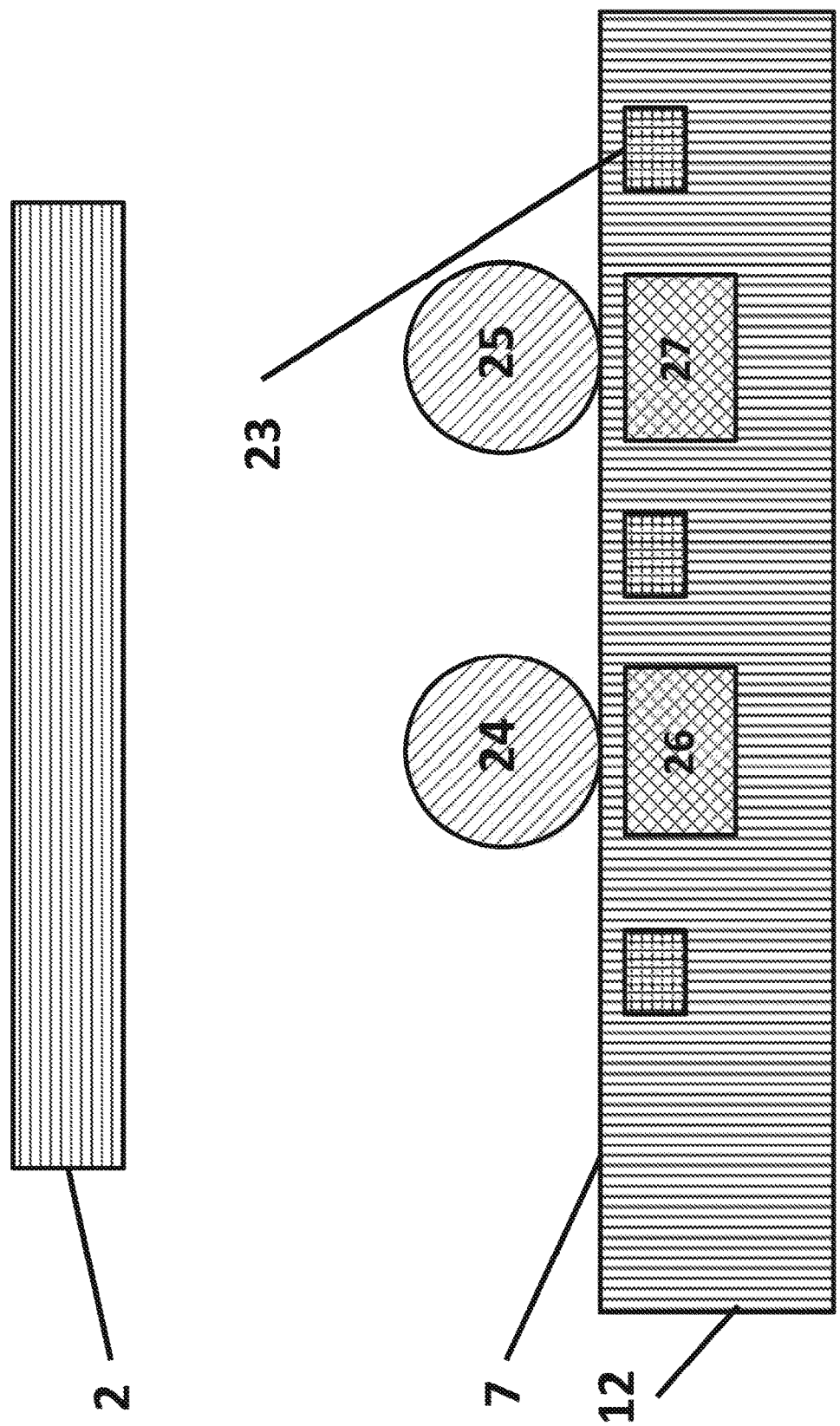
Figure 4C:
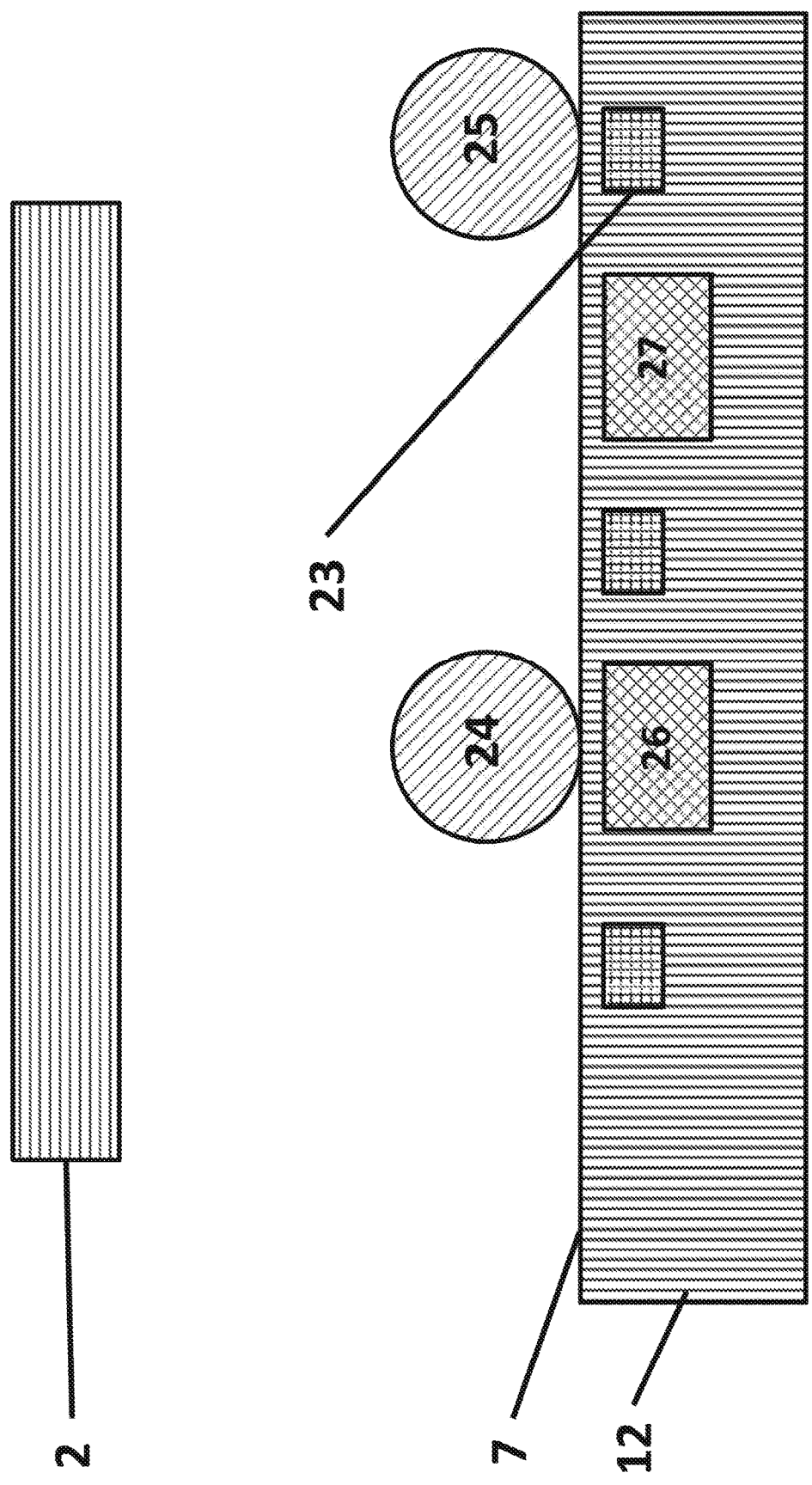
FIG. 4C is a cross-sectional view that presents the scenario from FIGS. 4A and 4B after non-specifically bound magnetic particle 25 is attracted to a separation conductor 23.

FIGS. 4A, 4B, and 4C show a top and a cross sectional view, respectively, of the light source 2 and the IC 12. One or more magnetic separation field generators can be embedded in the integrated circuit 12 at a lateral distance of 0.1 µm to 100 µm from the sensing area 21.

A portion of the magnetic particles 24 that sediment to the surface 7 of the IC 12 and may bind strongly through specific bio-chemical or inorganic interactions to the surface 7 of the IC 12. A portion of the magnetic particles 25 that sediment to the surface 7 of the IC 12 may bind weakly to the surface 7 of the IC 12 through non-specific interactions.

The assay can be performed in various assay formats. In a capture assay format, the presence of one or more target analytes would promote specific binding of the particles 4 to the surface 7 of the IC 12. In a competitive assay format, the presence of one or more target analytes would inhibit specific binding of the particles 4 to the surface 7 of the IC 12. In a derivative capture format, one or more by-products of one or more reactions with the target analyte would promote specific binding of the particles 4 to the surface 7 of the IC 12. In a derivative competitive format, one or more byproducts of one or more reactions with the target analyte would inhibit specific binding of the particles 4 to the surface 7 of the IC 12. Multiple assay formats can be performed concurrently on the same chip 12, or on the same assay system 10 with multiple chips. Electrodes and other bio-sensors can be integrated on the same chip to detect ions, electrolytes and general chemistry analytes.

The magnetic separation field generators can be used to remove the non-specifically bound magnetic particles from the sensing areas 21 so that the optical sensors 20 only detect specifically bound magnetic particles. The magnetic separation field generators can be implemented as electrical separation conductors 23 embedded in the integrated circuit 12 and routed in proximity to the sensing area 21. Current passing through the separation conductors generates magnetic forces that act on the magnetic particles inside the sensing area. The current can be from 0.01 mA to 200 mA depending on the separation force desired. A value for the current passing though separation conductors to separate 2.8 µm magnetic particles can range from 1 mA to 100 mA. The separation conductors 23 on either side of the sensing area 21 can be activated at different times in order to pull the magnetic particles. The current can be toggled between the two separation conductors at a frequency from 0.001 Hz to 100 MHz. The magnetic separation forces can be strong enough to displace non-specifically bound magnetic particles from the sensing area towards the separation conductor, but not strong enough to displace specifically bound magnetic particles. A sequence of magnetic separation forces is a series of magnetic forces resulting from modulating one or more currents through one or more magnetic separation conductors. The sequence of magnetic separation forces can be controlled by an algorithm stored on the IC 12.

Non-specific binding forces may be on the order of 0.1 pN to 10 pN, while specific binding forces may be on the order of 20 pN to 20 nN. For example, magnetic particle 24 may sediment over optical sensor 26 and may specifically bind to the surface 7 of the IC 12 over optical sensor 26. Thus, magnetic particle 24 may not be removed by the separation force generated by a separation conductor 23 placed laterally to the sensing area 21 and may be detected by optical sensor 26. On the other hand, magnetic particle 25 may sediment over optical sensor 27 and may not bind specifically (i.e., non-specifically bound) to the surface 7 of the IC 12 over optical sensor 27. Thus, magnetic particle 25 may be removed by the separation force generated by the conductors placed laterally to the sensing area 21 and may not be detected by optical sensor 27. The electric currents used to generate magnetic forces may be pre-programmed onto the IC 12 during the design process or after fabrication and may be adjusted at a later stage (e.g., before the assay or dynamically during the operation of the assay) depending on various parameters (e.g., temperature, viscosity of the aqueous sample 5, magnetic content of the magnetic particles, size/shape of the magnetic particles, and other factors). Magnetic forces can be generated externally to the integrated circuit 12 using one or more permanent magnets or external electromagnets (e.g., coils integrated onto the PCB 9). In a variation of the assay system 10, magnetic separation field generators may be omitted altogether from the IC 12.

FIG. 5A is a cross sectional side view of the dry sphere 3 placed in a cuvette 30 with vertical side walls 32. The cuvette can be of any shape including square, rectangular, cylindrical and can be smaller, greater or equal to the volume of the dried sphere 3. The cuvette 30 can also be equal to or slightly narrower than the diameter of the dried sphere 3 in order to hold it motionless in place. The cuvette 30 can be wider than the dry sphere 3.

To promote the complete dissolution of the dried sphere 3, the cuvette 30 can fill completely with the aqueous sample 5 as shown in FIG. 5B. The fill stop structure 31 can be an enlarging of the cuvette, a stop gap or a stop material.

To promote complete dried sphere 3 dissolution, the diameter of the dried sphere 3 can be similar to the diameter of the sedimentation capillary 13. For example the diameter of the dried sphere 3 can be between 25% and 50%, between 50% and 75%, between 75% and 850%, between 85% and 100%, between 100% and 115%, between 115% and 125%, between 125% and 150% or between 150% and 200% of the diameter of the sedimentation capillary 13.

To promote complete dry sphere 3 dissolution, the depth of the cuvette can be similar to the diameter of the dried sphere. For example the depth of the cuvette 30 can be between 10% and 25%, between 25% and 50%, between 50% and 75%, between 75% and 100%, between 100% and 125%, between 125% and 150% or between 150% and 200% of the diameter of the dried sphere 3. The cuvette 30 can be partially filled with the aqueous sample 5 or the cuvette can remain unfilled with the dry sphere 3 dissolving fully into the sedimentation capillary 13 below without any fluid entering the cuvette 30.

FIG. 5C shows the bottom of the cuvette acting as the fill stop structure.

FIG. 6 is a cross sectional side view of a cuvette with tapered side walls 40. The tapered sidewalls can hold the dried sphere 3 in place firmly. The tapered sidewalls 40 can be designed to wick the aqueous solution 5 via capillary force up the entire length of the tapered sidewall 40, or up a portion of the tapered sidewall 40. The tapered sidewalls 40 can be made to prohibit the wicking of the aqueous solution 5.

FIG. 7 is a cross sectional side view of a cuvette 30 with a cover 50 to hold the dried sphere 3 stationary. The cover 50 can be manufactured of a breathable or porous material to let air pass, or can be fully or partially hermetic to eliminate or reduce evaporation of the aqueous sample through the top of the sedimentation capillary 13. In the case that the cover 50 is hermetic, an air opening 51 can be implemented to let the trapped air evacuate as the aqueous solution 5 approaches. The air opening can be designed into the SPDM 8 or into the cover 50. The cover 50 can also be transparent or partially transparent to let light illuminate the dry sphere 3 and down the sedimentation capillary 13 after the dry sphere 3 dissolves. In this case, the optical sensors embedded in the IC 9 can detect when the dry sphere 3 has dissolved. The cover 50 can press on the dry sphere 3 in order to keep it motionless in the cuvette. To eliminate adhesion of the dry sphere 3 to the cover 50, the bottom of the cover 50 inside the cuvette 30 can be made adhesion free. The cover can be glued, taped, thermally bonded, or snap fit into location.

Figure 8:
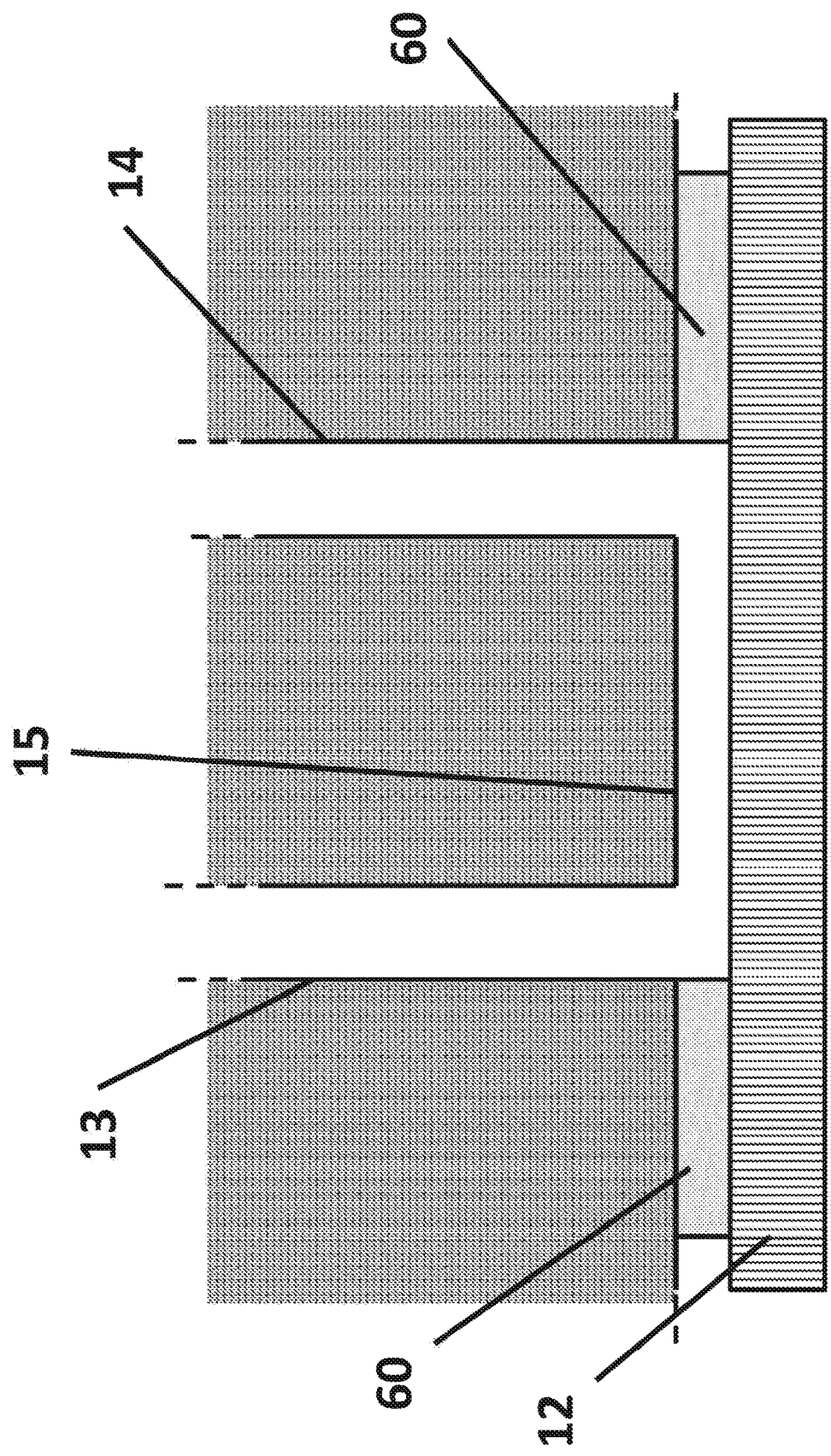
FIG. 8 is a cross sectional side view of the surface capillary 15 constructed from double sided tape 60.

FIG. 8 is a cross sectional side view of the surface capillary 15 constructed from double sided tape 60. A channel can be cut, punched or milled into double sided tape 60 or transfer adhesive or epoxy and that channel can form the sidewalls of the surface capillary 15.

The double sided tape 60 can provide a hermetic seal on the surface of the chip 12. The surface 7 of the IC 12 can be smaller than the bottom surface of the SPDM in such a way that the bottom surface of the SPDM completely overlaps the surface 7 of IC 12. Otherwise, any undesirable gaps in the double sided tape 60 could result in persistent leaks that can pool on the surface 7 of the IC 12.

The double sided tape 60 may be replaced by or used in combination with other adhesives such as silicones, acrylates, epoxies or others. A compression seal can be used instead of or in combination with adhesives; in this case, the double sided tape 60 may be replaced by a flexible gasket, and mechanical pressure could form the seal between the IC 10 and the SPDM 8. Alternatively, the SPDM could be made out of flexible material such as rubber or silicone, and the surface capillary 15 could be formed in the bottom surface of the SPDM, without any gasket or tape. The height of the double sided tape 60 or transfer adhesive can be less than 250 µm, for example between 1 µm and 10 µm, or 10 µm and 25 µm, or 25 µm and 50 µm, or 50 µm and 100 µm or 100 µm and 250 µm. A thinner adhesive reduces the void volume of the surface capillary 15 and bring the aqueous samples 5 in closer proximity to the surface 7 of the IC 12 for on-chip pre-treatment of the aqueous sample 5. A thick tape can be used to ensure a hermetic seal despite non uniformities on the surface 7 of the IC 12 or on the bottom interface of the SPDM 8.

Figure 9:
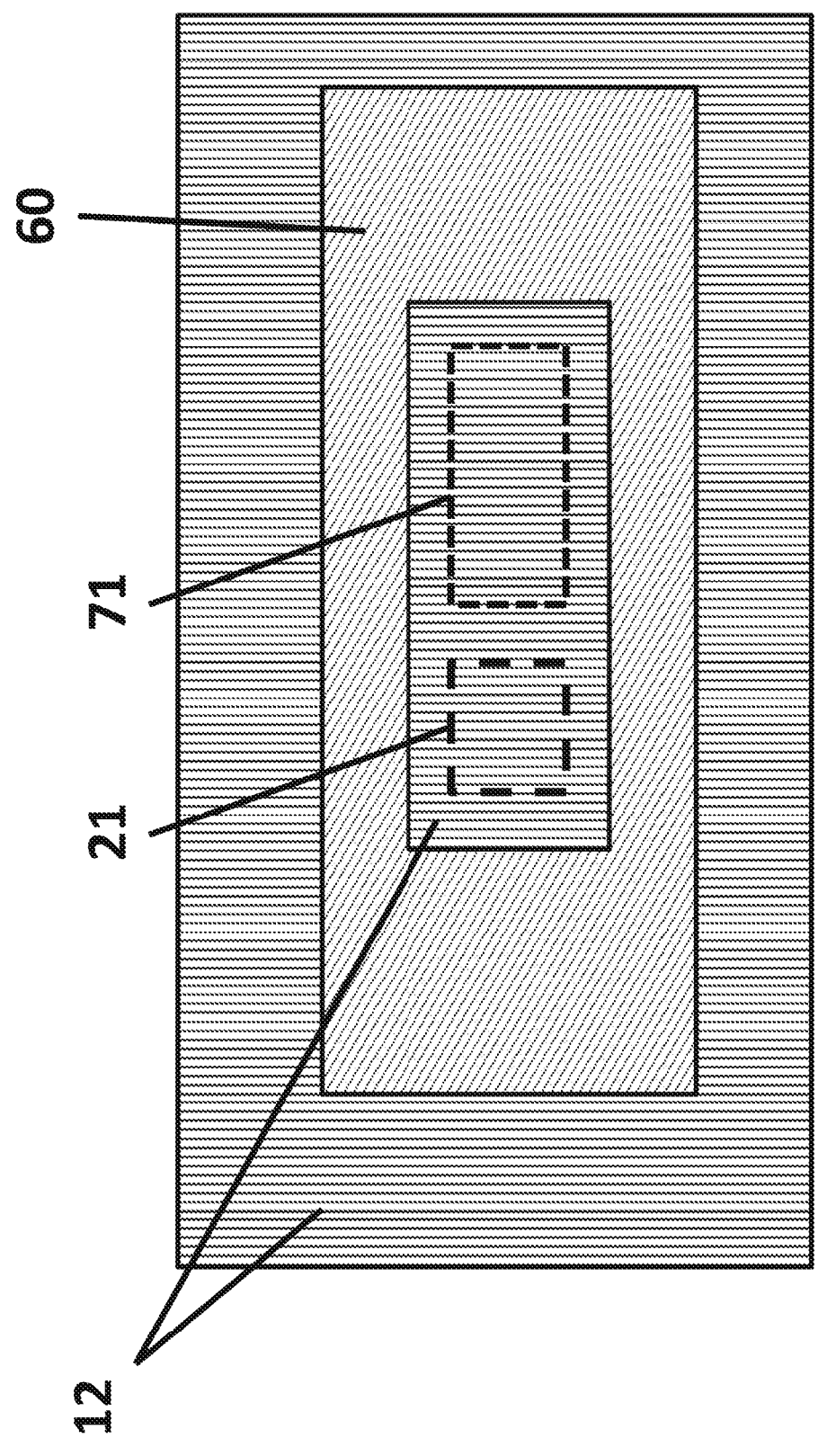
FIG. 9 is a top view of the surface of the integrated circuit 12 with the double sided tape 60 mounted on it. The sensing area 21 can be situated under the sedimentation capillary, while the active area 71 can be situated along the length of the surface capillary.

FIG. 9 is a top view of the surface of the integrated circuit 12 with the double sided tape 60 mounted on it. The sensing area 21 can be situated under the sedimentation capillary 13, while the active area 71 can be situated along the length of the surface capillary 15. Under the active area, a number of solid state devices can be integrated for the pre-treatment of the aqueous sample 5 as it flow by into the sedimentation capillary 13. One or more temperature sensors and heating elements can be embedded under the active area 71 to heat the aqueous sample 5 as it flows by and measured the temperature of sample 5. The temperature of the SPDM or the temperature of the aqueous sample in the SPDM can be adjusted and kept at constant temperature for isothermal nucleic amplification of oligonucleotides, or the temperature can be cycled for PCR amplification of oligonucleotides. Similarly, one or more pH sensors and hydrolysis electrodes or other pH adjusting elements can be embedded under the active area 71 to respectively measure and adjust the pH of the aqueous sample 5. The pH of the aqueous sample in the SPDM can be adjusted kept constant for analyte analysis, or the pH can be cycled to promote certain reactions. Moisture sensors, blood cell counters and other solid state sensor and actuators can be embedded under active area.

Heating elements can be placed under a portion of the active area 71 or under a portion of sedimentation capillary 13. Heating elements can be placed under the entire active area 71 or under the entire sedimentation capillary 13 but only a portion can be activated. Heating elements embedded under surface 7 of the IC 12 can be used to create eddy currents or convection currents to mix the magnetic particles in solution. Heating elements under a portion of the sedimentation capillary 13 can heat fluid in proximity. The rising heated fluid from a portion of the sedimentation capillary can generate eddy currents or convection currents that keep the magnetic particles in suspension and incubating with the target in the sedimentation capillary. The heating elements can be enabled before the dry sphere 3 dissolves or after the dry sphere dissolves.

Figure 10:
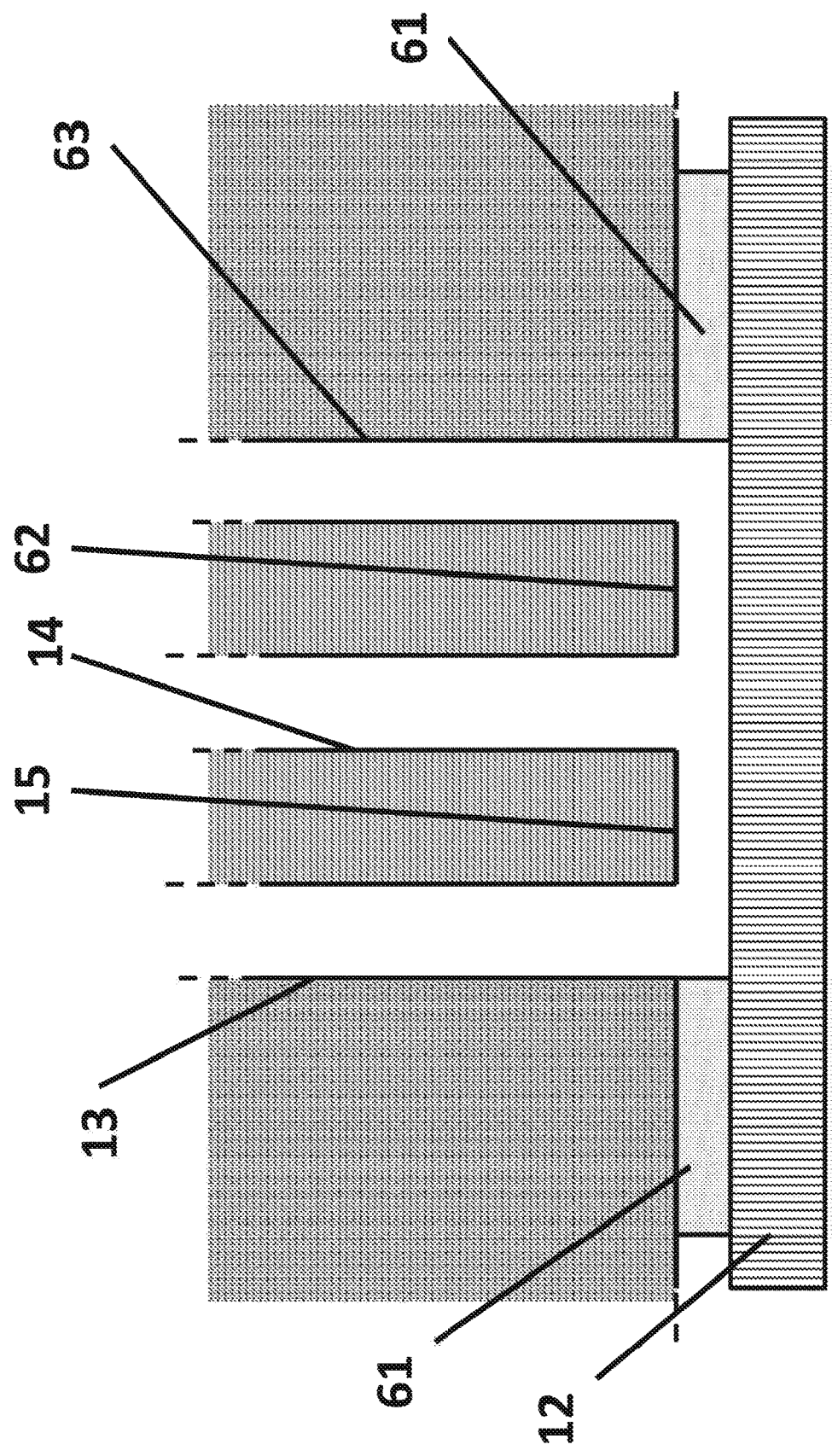
FIG. 10 shows a cross of the system with a delivery capillary 14 leading to two surface capillaries 15 and 62, which lead to two sedimentation capillaries 13 and 63, respectively, for controls or multiplexed operation.

FIG. 10 shows a cross section of the system with delivery capillary 14 leading to a first surface capillary 15 and a second surface capillary 62. Surface capillary 15 leads to a first sedimentation capillary 13 and surface capillary 62 leads to a second sedimentation capillary 63. Each sedimentation capillary can have a different dried sphere at the top. The surface of the sensing areas below each sedimentation capillary can have different functional chemistry coatings. In this system, multiple assays can be performed simultaneously without mixing between the sedimentation capillaries. The heights of the different sedimentation capillaries can be different and can be tailored to the incubation time necessary for the assay being performed in the sedimentation capillary. More than one assay can be performed in one sedimentation capillary. More than two surface capillaries leading to more than two sedimentation capillaries can be integrated on the same system. The surface capillaries can be connected in a star network, an H-network or any other network of surface capillaries allowing the aqueous sample to flow from one or more filters through one or more delivery capillaries to reach one or more sedimentation capillaries.

To minimize the amount of sample and the number of applications, all the surface capillaries can share the same delivery capillary and the same filter. One or more sedimentation capillaries can be reserved exclusively for performing assay controls.

To ensuring proper functioning of all assay components, conventional non-quantitative immunoassays rely on negative controls using an irrelevant antibody of the same isotype to determine the non-specific signal or background, and positive controls using anti-species antibodies to generate a positive signal.

Quantitative immunoassays rely on calibrators—known quantities of analyte (calibrators) in a synthetic matrix—to quantify unknowns.

This fully integrated assay system 10 can use a sample specific internal assay calibration that relies on the sample matrix itself to extrapolate the background signal and the native target signal.

To calibrate the native target signal resulting from the native target concentration in the aqueous sample 5, the assay system can contain two sedimentation capillaries 13 and 63, that may or may not be fluidically connected to the same delivery capillary 14. A pre-determined quantity of a dry calibrant consisting of lyophilized synthetic target or target derivative, or target analogue, can be added in the dry sphere at the top of sedimentation capillary 63, along the sides of sedimentation capillary 63, on the surface 7 of the chip 12 at the bottom of sedimentation capillary 63, in the surface capillary 62 leading to sedimentation capillary 63, or on the surface 7 of the chip 12 in the surface capillary 62. The preferred location for the dry calibrant is on the surface 7 of the chip 12 in the surface capillary 62 since the lyophilized target can be deposited at the same time as the sensing area is being coated, and since it enters into the sedimentation capillary 62 in a dissolved state, akin to the native target. The surface capillary 62 cannot flow into sedimentation capillary 13 since the dry calibrant would corrupt the detection of the native target signal. The dry calibrant will be rehydrated by the sample and flow into the sedimentation capillary 63. The quantity of dry calibrant in sedimentation capillary 63 can be between 1 zeptogram and 1 attogram, between 1 attogram and 1 femtogram, between 1 femtogram and 1 picogram, between 1 picogram and 1 nanogram or between 1 nanogram and 1 microgram. A different quantity 2 of dry calibrant, or no dry calibrant, can be loaded in the dry sphere at the top of sedimentation capillary 13, along the sides of sedimentation capillary 13, on the surface 7 of the chip 12 at the bottom of sedimentation capillary 13, in the surface capillary 15 leading to sedimentation capillary 13, or on the surface 7 of the chip 12 in the surface capillary 15. The difference in signals in the two sedimentation capillaries 13 and 63, i.e. the difference in the number of specifically bound magnetic particles in sedimentation capillaries 13 and 63 can be used to calibrate the native target signal resulting from the native target concentration in the sample by a signal calibration mathematical operation. The signal calibration mathematical operation can include addition, subtraction, multiplication, division, non-linear correlation through look-up tables and can be performed digitally on the chip 12. An arithmetic logic unit can be integrated on the chip 12 to perform the signal calibration mathematical operation. The sedimentation capillaries 13 and 63 must be positioned to avoid the dry calibrant intended to flow into sedimentation capillary 63 from diffusion or traveling or flowing to sedimentation capillary 13 and to avoid the dry calibrant intended to flow in sedimentation capillary 13 from diffusion or traveling or flowing to sedimentation capillary 63. The height of capillary 63 can be shorter than capillary 13 to minimize the amount of sample volume needed to calibrate the native target signal.

To calculate the background signal, i.e. the abnormally strongly bound magnetic particles resulting from undesirable non-specific interactions, the system can contain a first sedimentation capillaries 13 and a third sedimentation capillary 64. The sedimentation capillary 64 can have a different height than sedimentation capillary 13 resulting in a different sedimentation times and by extension incubation time. In so doing, the number of specifically bound magnetic particles resulting from the native target concentration in the sample will be different in sedimentation capillary 13 versus sedimentation capillary 64 due to the different incubation times. Meanwhile, the background signal, or the number of non-specifically bound magnetic particles will remain approximately equal. The difference in the number of bound magnetic particles, both specifically and background non-specifically, in sedimentation capillaries 13 and 64 can be used to determine the number of background non-specifically bound magnetic particles by a background calculation mathematical operation. That background calculation mathematical operation can include addition, subtraction, multiplication, division, non-linear correlation through look-up tables and can be performed digitally on the chip 12. An arithmetic logic unit can be integrated on the chip 12 to perform the background calculation mathematical operation.

The native target signal is correlated to the magnetic bead settling time, i.e. the incubation time, while the background signal remains approximately constant with incubation time. To measure the background signal, 2 concurrent assays, Assay 1 and Assay 2, can be run in two different sedimentation capillaries with different heights, corresponding to for example 12 and 2 minutes incubation times respectively. Assay 1 bead count B1 consists of a background signal Bkg and a native target signal component Sig1: B1=Bkg+Sig1. Similarly, Assay 2 bead count B2 consists of the same background signal Bkg but with a different native target signal Sig1: B2=Bkg+Sig2, where Sig1 equals approximately 6 Sig2 according to the ratio of the incubation times. The background signal and the native target signals can easily be extracted arithmetically: Sig1=(B1−B2)*(6/5), Bkg=B1−Sig1, and Sig2=B2−Bkg. Note that the two incubation times depend on the heights h1 and h2 of the chambers and their ratio can be controlled tightly by design, irrespective of sample viscosity. The ratio of h1 to h2 can be increased as much as possible for more precise measurement of the background signal. The ratio can be between 1:1 and 1.5:1, between 1.5:1 to 2:1, between 2:1 and 4:1, between 4:1 and 8:1, between 8:1 and 16:1, between 16:1 and 100:1.

More than 2 sedimentation capillaries can be implemented on the same assay system 10 to perform native target signal calibration and background non-specifically bound magnetic particles calculation from the same aqueous sample 5. Three sedimentation capillaries can be used per analyte. A first sedimentation capillary can be used to perform the standard assay, a second sedimentation capillary can be used to measure the background signal, while a predetermined amount of a dry calibrant can be spiked into the surface capillary leading to a third sedimentation capillary, which can be used to calibrate the native target signal.

In a multiplexed format, the sedimentation capillaries can be grouped to minimize the total amount of volume of aqueous sample 5 needed. Multiple background signal measurements for multiple analytes can be performed using the same sedimentation capillaries, while multiple native signal calibrations for multiple analytes can be performed using the same sedimentation capillaries. Native signal calibration for a first analyte and background measurement for a second analyte can be performed using the same sedimentation capillary.

The background signal measurement and native target signal measurement can also be used qualitatively to invalidate the test for example should they fall outside expected ranges. The background signal measurement and native target measurement can be performed on more than one targets concurrently or in series on the same system or moreover on the same chip.

For qualitative yes/no measurements, the background signal measurement and the native target signal calibration can be performed using a single sedimentation capillary 63 to minimize the volume of aqueous sample 5 needed. In this case, the height of sedimentation capillary 63 can be a ratio r of the height of sedimentation capillary 13. Sedimentation capillary 63 can contain the dissolved dry calibrant. The bead counts in the sedimentation capillaries 13 and 63 is given respective by B1=Sig1+Bkg and B2=Sig2+Bkg+Cal. The difference between the bead counts is given by B1−B2=Sig1+Bkg−Sig2−Bkg−Cal. Sig1 and Sig2 are ratioed according to the ratio r of the heights of the sedimentation capillaries 13 and 63 and Cal is the solubilized dry calibrant concentration in sedimentation capillary 63. B1−B2=Sig1*(1−r)−Cal. The amount of dry calibrant can chosen to be so that the concentration of resolubilized dry calibrant in sedimentation capillary 63 is equal to a qualitative concentration threshold multiplied by (1−r). B1−B2=Sig*(1−r)−Threshold*(1−r). As a results B1>B2 when Sig>Threshold and B2>B1 when Sig<Threshold.

The bead count to target concentration relationship is non-linear so additional calculation can be performed when assay system operates in the non-linear slope of the bead count to concentration curve. The IC 12 can perform the non-linear calculation or store a look-up table with the relationship to convert between bead count and target concentration and back. Target concentration refers to native target and calibrant concentration.

The on-chip generated magnetic separation forces can be adjusted such that the background signal is zero beads. In this case, no measurement of the background signal is needed.

Figure 11:
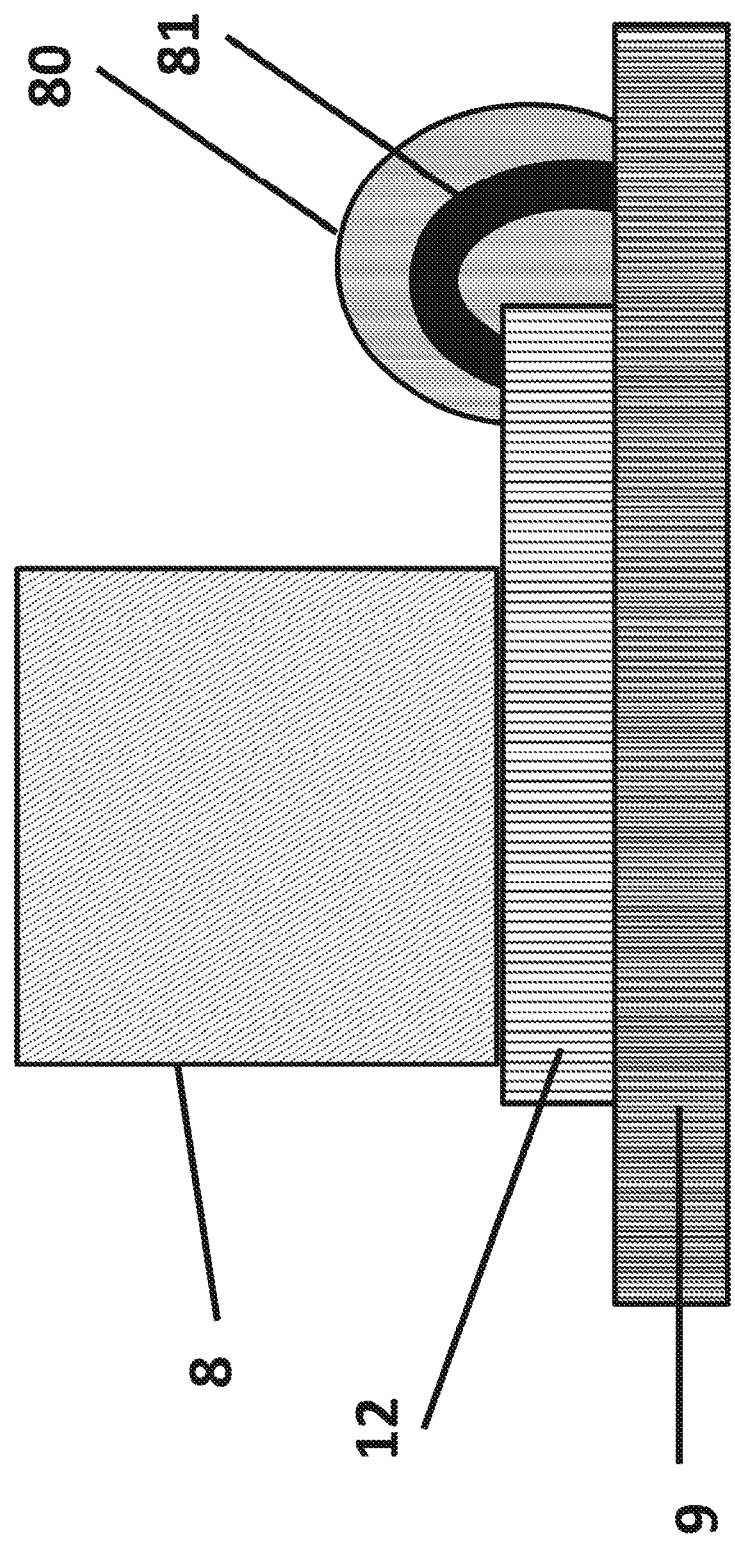
FIG. 11 shows a cross section of the integrated circuit 12 mounted onto the PCB 9 and electrically connected via a wirebond 81. The wirebond 81 can be hermetically sealed by encapsulant 80.

FIG. 11 shows a cross section of the integrated circuit 12 mounted onto the PCB 9 and electrically connected via a wirebond 81. The wirebond 81 can be hermetically sealed by encapsulant 80. The SPDM 8 can be placed directly on the exposed surface 7 of the IC 12. The encapsulant can be an epoxy, acylate, urethanes, silicones or other adhesives.

Figure 12:
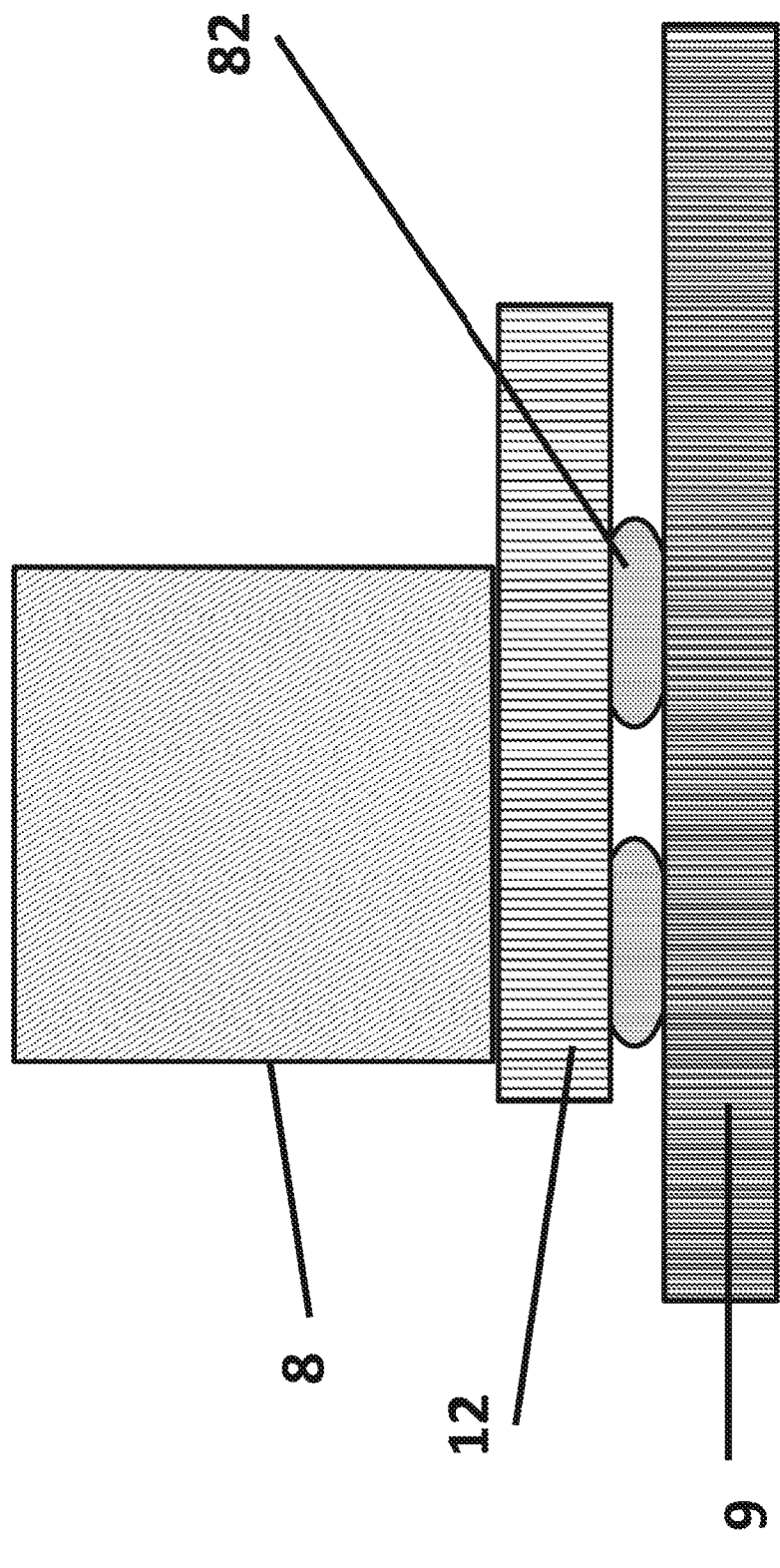
FIG. 12 shows a cross section of the integrated circuit 12 mounted onto the PCB 9 and electrically connected by way of one or more through-silicon vias 82.

FIG. 12 shows a cross section of the integrated circuit 12 mounted onto the PCB 9 and electrically connected by way of one or more through silicon vias 82. The use of through silicon vias which can be placed under the active sensing area can minimize the area of the IC 12 devoted to pads or input/output functions and by extension minimize the cost of IC 12. The SPDM 8 can be placed directly on the exposed surface 7 of the IC 12.

Figure 13:
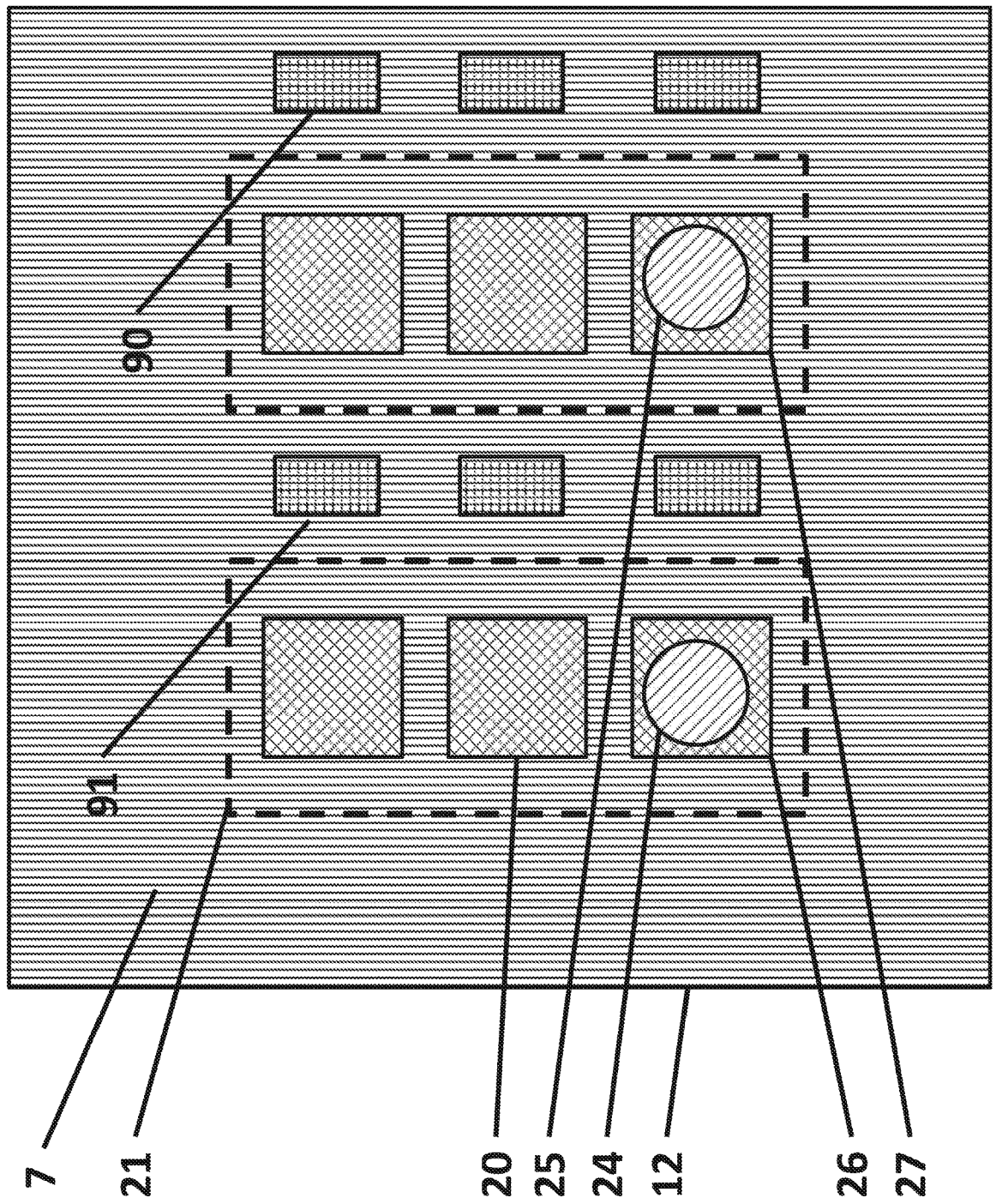
FIG. 13 shows the top view of the integrated circuit surface 7 with one digitally addressable separation conductor 90 per sensor.

FIG. 13 shows the top view of the integrated circuit surface 7 with one dedicated magnetic separation conductors 90 for each sensor 20. Each dedicated magnetic separation conductor can be individually addressed and activated. The current through each dedicated magnetic separation conductor can be precisely set to achieve the desired force on a magnetic particle 24 atop a sensor 26. When a magnetic particle lands on a sensor, it can be detected and the dedicated magnetic separation conductor can be used to remove it if it is non-specifically bound without disturbing other magnetic particles more than one sensor length away. The non-specifically bound magnetic particles can be removed one by one off their corresponding sensors by dedicated separation conductors for superior assay control and precision.

Each sensor can have more than one dedicated magnetic separation conductors. For example, each sensor can have two dedicated magnetic separation conductors, one on each side for bi-lateral magnetic separation. A dedicated magnetic separation conductor can be shared with one or more neighboring sensor.

Figure 14:
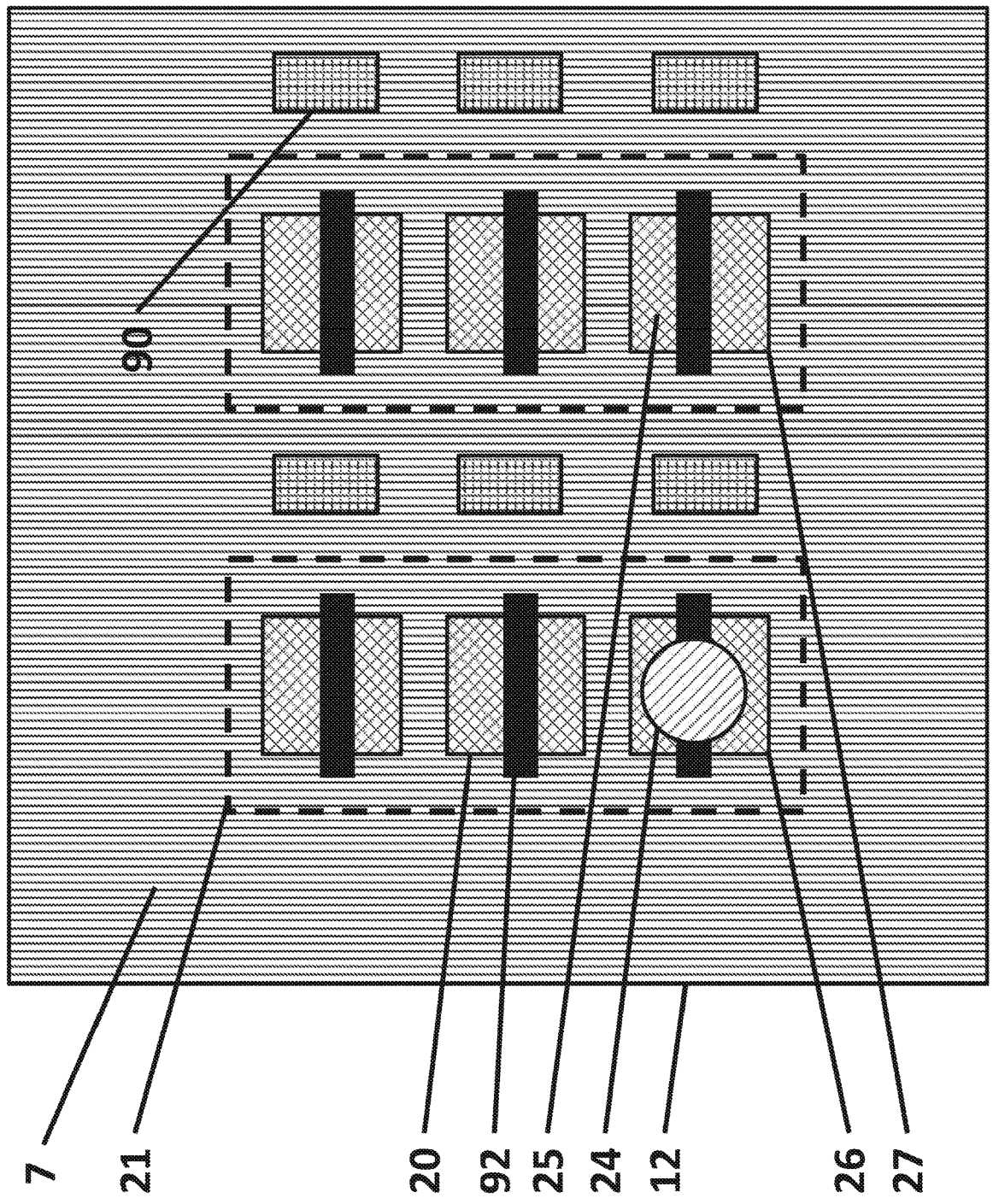
FIG. 14 shows the top view of the integrated circuit surface 7 with one digitally addressable separation conductor 90 and one digitally addressable concentration conductor 92 per sensor

FIG. 14 shows the top view of the integrated circuit surface 7 with one dedicated magnetic concentration conductor 92 for each sensor 20. Each dedicated magnetic concentration conductor 92 can be individually addressed and activated. The current through each dedicated magnetic concentration conductor can be precisely set to achieve the desired concentration force on a magnetic particle sedimenting atop a sensor 20. Magnetic particles can be pulled atop sensors by dedicated magnetic concentration conductor 92, and once the magnetic particle it atop the sensor, the dedicated magnetic concentration conductor can be switched off.

Each sensor can have more than one dedicated magnetic concentration conductors for rastering the magnetic particles. A dedicated magnetic concentration conductor can be shared with one or more neighboring sensor. Rastering is the process of moving or rolling a particle on the surface 7 of the IC 12 to promote specific binding.

The magnetic particles can be rastered on the surface by the dedicated concentration conductors and the dedicated separation conductors applying one or more magnetic rastering forces. On the flat X-Y planar surface 7 of the IC 12, the dedicated separation conductors can be arrayed in rows in the x-direction and the dedicated concentration conductors can be arrayed in columns in the y-direction. In so doing, non-specifically bound magnetic particles can be rastered 2-dimensionally in the positive and negative X and Y directions by a rastering algorithm that controls the movement of each particle individually, or one or more ensembles of particles. The particles can be rastered by on-chip generated magnetic rastering forces until they form a binding interaction on the surface 7 of the IC 12, preventing the particle from rastering further. A detection algorithm can detect when a particle is no longer rastering on the surface of the IC, and activate the magnetic separation forces. The magnetic separation forces can be applied and if the particle is non-specifically bound, the particle can be removed atop the sensor and continue to be rastered across the array. The magnetic separation force can be higher than the magnetic rastering force. The magnetic rastering force can be different from the magnetic concentration force. However, if a particle is specifically bound atop the sensor, then the sensor can detect the particle and the dedicated concentration and dedicated separation conductors for that sensor can be de-activated such that other particles are not pulled atop that sensor. The magnetic concentration forces can be used to pull the magnetic particles atop the sensors, to raster the magnetic particles across the sensor or to raster the magnetic particle on top of the sensor. In the latter case, the particle is detectable throughout the entire raster process. One or more magnetic concentration conductors can be placed directly atop a sensor or laterally spaced to a sensor. The optical sensors can be arrayed densely to ensure a 100% fill factor so that all the particles or ensembles of particles on the surface of the chip are detected.

When the particles 4 are released from dissolution of the dry sphere 3, they can disperse throughout the sedimentation capillary 13 and land on the surface 7 of the IC 12 at different times. In this scenario, the incubation time on the surface 7 of the IC 12 for a given particle 4 can vary depending on when it landed on the surface 7 of the IC 12. The magnitude of non-specific interactions can depend on the time the particle 4 lies on the surface 7 of the IC 12, leading to variability in the assay. To overcome this variability, a sequence of magnetic separation forces can be initiated at different magnetic separation times. The magnetic separation times can be determined dynamically at run-time or pre-determined and stored in memory. At each magnetic separation time, a sequence of magnetic separation forces can be applied to remove the non-specifically bound particles away from the sensors. Once the magnetic separation is complete, the sequence of magnetic separation forces can be deactivated until the next magnetic separation time to allow more particles to settle. The assay protocol can consist of more than one magnetic separation times with different or variable intervals between them. The intervals between magnetic separation times can vary from 5 seconds to 15 minutes, or from 30 seconds to 10 minutes, or from 1 to 5 minutes. The shorter the interval between magnetic separation times, the shorter the opportunity for the particles to land on the surface and bind specifically. The longer the interval between magnetic separation times, the more chance for abnormally strong non-specific interactions to form. The sequences of magnetic separation forces applied at each magnetic separation time can be different, for example in magnetic force magnitude, conductors activated, frequency of forces, length of application of forces, magnetic force profile and algorithm of activation of conductors.

The number of particles can be detected before and after a sequence of magnetic separation forces is applied. The specific particle binding ratio is the ratio of the pre-separation number of magnetic particles detected by the sensors before the magnetic separation forces are applied to the post-separation number of magnetic particles detected by the sensors after the magnetic separation forces are applied. The specific particle binding ratio is a useful indicator of binding since it eliminates or mitigates the dependence to the absolute number of particles that sedimented on the surface 7 of the IC 12.

The sequences of magnetic separation force can be tailored such that when applied, few magnetic particles—i.e. less than 1, or less than 10, or less than 100, or less than 1000, or less than 10000, or less than 1000000—can land on the sensor but rather the sedimenting particles can be pulled toward the separation conductor before they have the opportunity to land on the surface 7 of the IC 12. This way, the post-separation number can avoid being corrupted by non-specifically bound particles landing on the sensors during the application of the magnetic separation force.

When a sequence of magnetic separation forces is deactivated, the current through the respective separation conductors can be switched off and the magnetic particles can settle on the sensor indiscriminately, while during the magnetic separation sequence, few magnetic particles—i.e. less than 1, or less than 10, or less than 100, or less than 1000, or less than 10000, or less than 1000000—may be able to sediment on a sensor.

More than one sequence of magnetic separation forces generating separation forces on different areas of the IC 12 can be applied at the same magnetic separation times, or at different magnetic separation times. Multiple areas of the ICs can perform multiple assays independently.

An assay can consist of multiple magnetic sequences of magnetic separation forces initiated at multiple magnetic separation times. A final sequence of magnetic separation forces can be using stronger magnetic separation forces or magnetic separation forces for longer duration. A specific particle binding ratio can be calculated for each magnetic separation sequence, and the multiple specific binding ratios can be combined to give a final particle binding ration, which can correspond to the target analyte concentration in the aqueous sample 5.

A final particle binding ratio can be calculated by dividing the final number of particles detected by the total number of particles that sedimented onto the sensors. The total number of particles that sedimented onto the sensor is not straight-forward to calculate if prior magnetic separation sequences were applied before the final magnetic separation sequence. The total number of particles is equal to the sum of all the pre-separation particles counts 22 minus the sum of all the post-separation particle counts plus the final post-separation particle count.

The sequence of magnetic separation forces can include a magnetic force chirp, where the magnetic forces applied can be toggled between the left and right side of a sensor at increasing frequency. At the beginning of the magnetic chirp, strong separation forces strongly remove the non-specifically bound beads, while at the end of the magnetic chirp, the toggle frequency is too high for the particles to move away from the separation conductors. This prevents distant separation conductors from rastering non-specifically bound particles across sensors prior to detection.

The assay system 10 can provide different assay results at different times. Intermediate results can be provided ahead of final results. The intermediate results can include assay progress information and qualitative assay results before the final quantitative results are complete and displayed or transmitted. The intermediate results can provide expedited qualitative information.

The intermediate results of the assay after each intermediate sequence of magnetic separation forces can be displayed or transmitted for real-time updates. In this case, after each intermediate sequence of magnetic separation forces, the particle binding ratio can be arithmetically processed is if it were a final sequence of magnetic forces.

To expedite access to assay information, expedited qualitative results of the assay can be displayed or transmitted before the full assay is complete and before precise quantitative information is available. The relative particle binding ratio at the end of the first magnetic separation interval or any subsequent magnetic separation interval can be used to provide the expedited qualitative information.

An example of an on-chip assay protocol is given below:
1. IC 12 in standby until detection of aqueous sample on surface of IC under surface capillary. Once detected. IC 12 activates the heating elements to heat the aqueous sample to 37 C and proceed with protocol.
2. IC 12 waits until detect of aqueous sample on surface of IC 12 under sedimentation capillary 13. IC 12 proceeds with protocol when detected or send error message if timed out.
3. IC 12 detects dissolution of dry sphere by changes in light on sensing area 21.
4. IC 12 activates magnetic concentration conductors.
5. IC 12 waits 2 minutes.
6. IC 12 reads out each sensor and counts the pre-separation number of particles to give Count 1.
7. IC 12 de-activates magnetic concentration conductors.
8. IC 12 activates the first sequence of magnetic separation forces to remove all the non-specifically bound particles from the sensor surfaces.
9. IC 12 reads out each sensor and counts the post-separation number of particles to give Count 2.
10. IC 12 calculated ratio of Count 2/Count 1 and correlates ratio to a concentration.
11. IC 12 displays the concentration or the qualitative information.

Protocol elements 4-10 can be repeated until all the particles have settled onto the surface of the chip. In each repeat of protocol elements 4-10, the magnetic concentration forces and separation forces can be varied. A Cumulative Pre-Counts and a Cumulative Post-Count can be the sum of all the pre-separation counts and all the post-separation counts, respectively. The different pre-separation counts and post-separation counts from each sequence of magnetic separation forces can be combined arithmetically to give a final particle count and a final binding ratio. In protocol element 11, the correlation function that translates the final particle count or final binding ratio to a concentration of target analyte can be stored on chip from values obtained during manufacturing. The correlation function can also include the results from the background measurement and the native target signal calibration. The assay can be initiated by the humidity or moisture sensors, or the assay can be initiated by a button or a touch screen integrated in the assay system 10.

When detecting a particle, the optical sensors can internally perform correlated double sampling to a calibration value acquired during manufacturing, or to a value obtained in real time running the assay. The optical sensor can measure the optical signal before and after a particle lands on the sensor. The difference or the ratio can be compared to a threshold to determine whether a particle is present. The sensor can detect the optical signal before and after magnetic separation to detect the removal of a particle.

Figure 15:
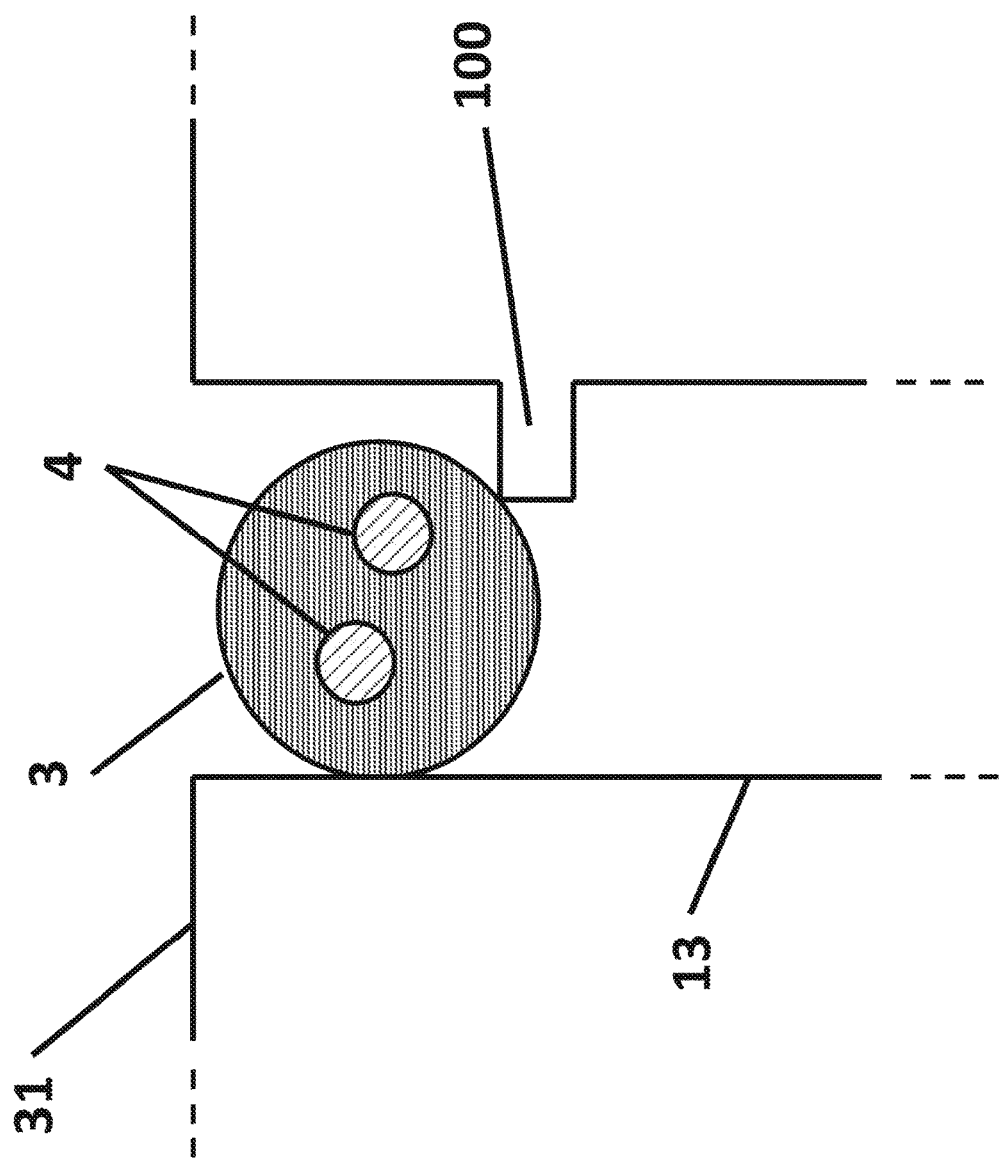
FIG. 15 shows the cross section of the sedimentation capillary 13 with a notch 100 to retain the dried sphere 3 in the sedimentation capillary 3.

FIG. 15 shows the cross section of the sedimentation capillary 13 with a notch 100 to prevent the dried sphere 3 falling into the sedimentation capillary 13. The dried sphere 3 can have smaller diameter than the sedimentation capillary 13 but can be large enough to be prevented by the notch 100 from falling into the sedimentation capillary.

Figure 16:
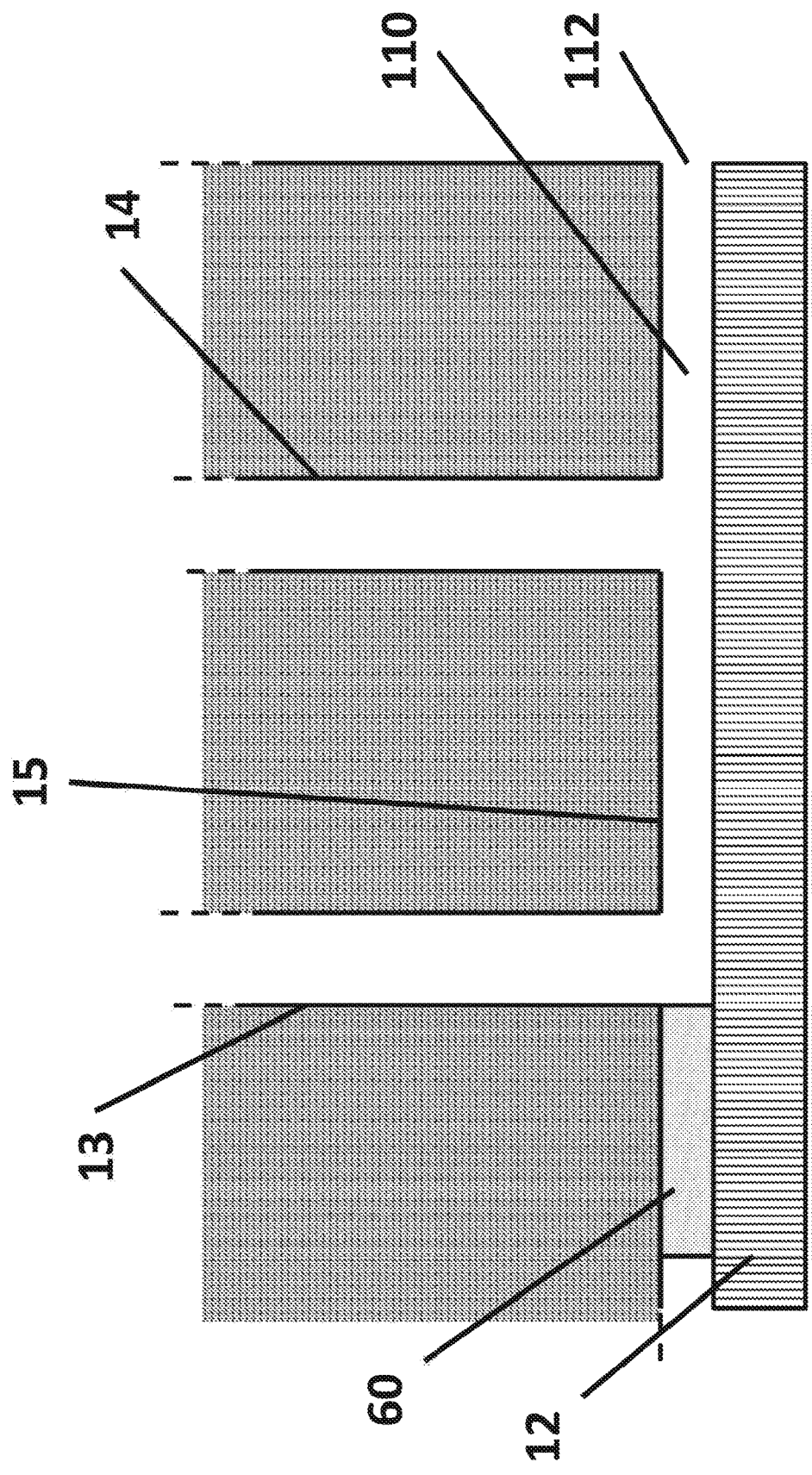
FIG. 16 shows the cross sectional view of the delivery capillary 14, the surface capillary 15 and the sedimentation capillary 13 and passive unidirectional valve that prevent the suck-back of aqueous sample from the sedimentation capillary to the filter.

FIG. 16 shows a cross section of the delivery capillary 14, the surface capillary 15 and the sedimentation capillary 13 atop the IC 12. When a small volume of aqueous sample 5 is applied (i.e. less than 200 ul, or less than 100 ul, or less than 50 ul or less than 30 ul or less than 20 ul, or less than 10 ul, or less than 5 ul, or less than 2 ul or less than 1 ul), the evaporation of the aqueous sample 5 can results in small fluidic flows that can disturb the assay on the surface 7 of the chip 12. To reduce or eliminate evaporation through the top of the sedimentation capillary 13, the cover 50 can be made or a material that reduces or eliminates evaporation. Moreover, the air opening 51 can be small enough in cross section to limit by diffusion or other effects the amount of aqueous sample 5 that can evaporate through it.

A second source of evaporation can occur through the filter 6. In this case a "suck-back" pressure (vacuum) can be generated as the aqueous sample evaporates from the filter surface. The filter has a large surface area and can evaporate fluid at a high rate. When a small amount of sample is applied, the aqueous sample 5 can traverse the filter into the delivery capillary 14, into the surface capillary 15 and into the sedimentation capillary 13, but can be sucked back through the filter due to evaporation before the full assay can be performed. This can be overcome by a lid that can close over the sample port on assay system 10 after the aqueous sample 5 has been applied and eliminate or reduce the amount of aqueous sample 5 that evaporates into the surrounding environment.

Another way of mitigating the evaporation through the top of the filter 6 is to implement a passive unidirectional valve in the filter 6, or in the delivery capillary 14, or in the surface capillary 15, or in the sedimentation capillary 13 or at the top of the sedimentation capillary 13 or at the top of the cuvette 30. The passive unidirectional valve can allow the fluid to flow from the filter 6 to the delivery capillary 14, or to the surface capillary 15, or to the sedimentation capillary 13, or to the top of the sedimentation capillary 13 or to the top of the cuvette 30 but not in the reverse direction. The passive unidirectional valve can eliminate or reduce the "suck-back" flow resulting from aqueous sample evaporation through the filter 6.

For ease of use of the assay system 10, a passive unidirectional valve rather than an actuated unidirectional valve is desirable. A Martin vent 110 is a passive unidirectional valve that can relieve the "suck-back" pressure with air. The Martin vent 110 provides a low impedance path for air to be sucked back towards the filter without passing through the sedimentation capillary 13, thereby leaving the fluid in the sedimentation capillary 13 intact and the assay able to complete unmolested. To prevent the aqueous sample 5 from leaking out of the Martin vent, a microfluidic stop gap 112 or fluid trap can be implemented at the terminus of the Martin vent 110. The design of this microfluidic stop gap can be such that its surface tension in the direction of the filter is less than the surface tension in the sedimentation capillary or in the cuvette in the direction of the filter such that air will preferentially flow from the Martin vent as opposed to the cuvette or sedimentation capillary.

The Martin vent can be placed anywhere along the length of the delivery capillary or surface capillary that prevents a "suck-back" pressure being generated by the filter when the fluid in the filter begins to evaporate from pulling or sucking back the fluid in the SPDM. Alternatively, a microfluidic check valve may be placed anywhere between the outlet of the filter and the sedimentation capillary.

Figure 17A:
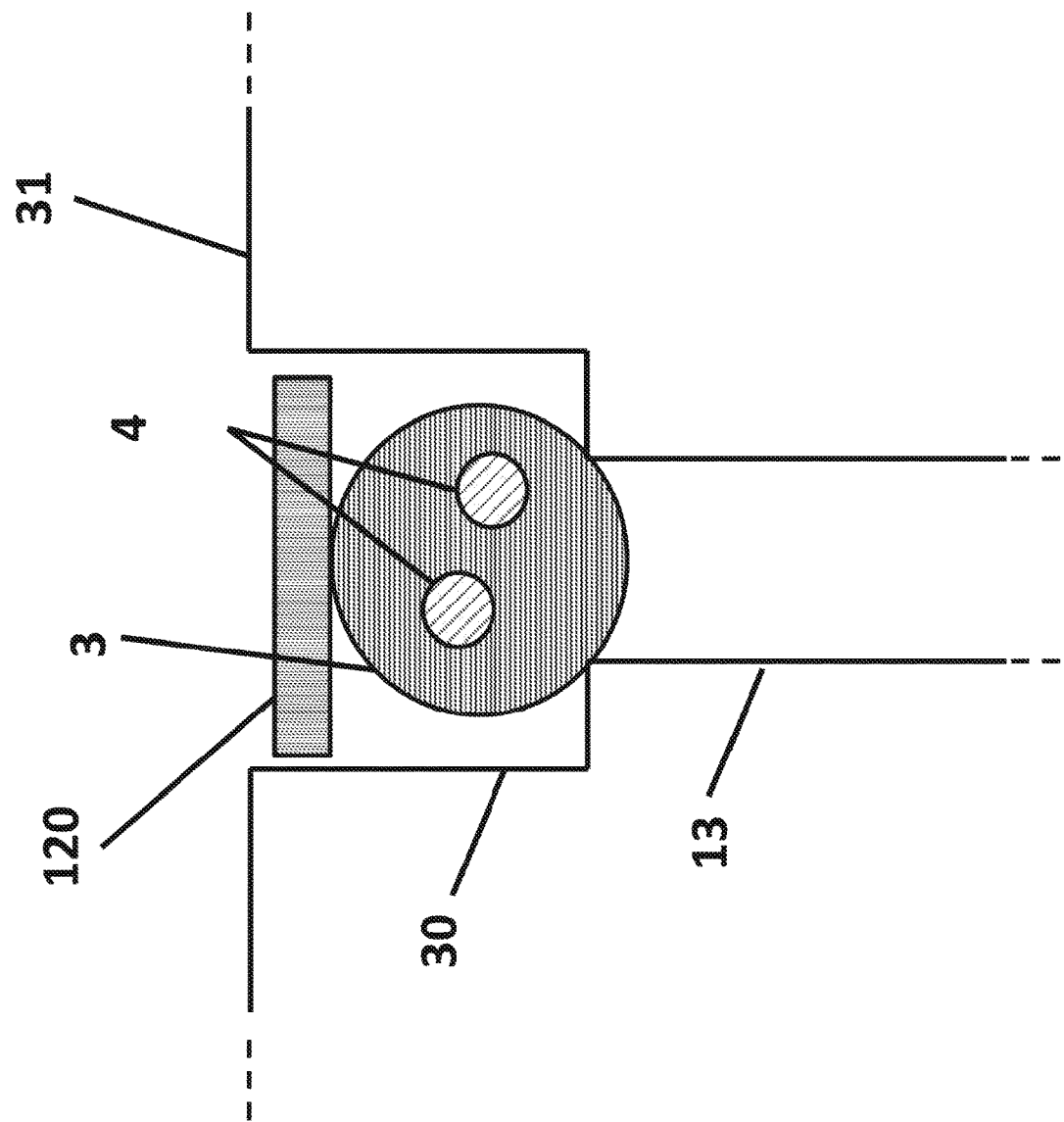
FIG. 17A is a cross-sectional side view of a flow stop 120 placed above the dry sphere 3, before the aqueous sample 5 has dissolved the dry sphere 3.
Figure 17B:
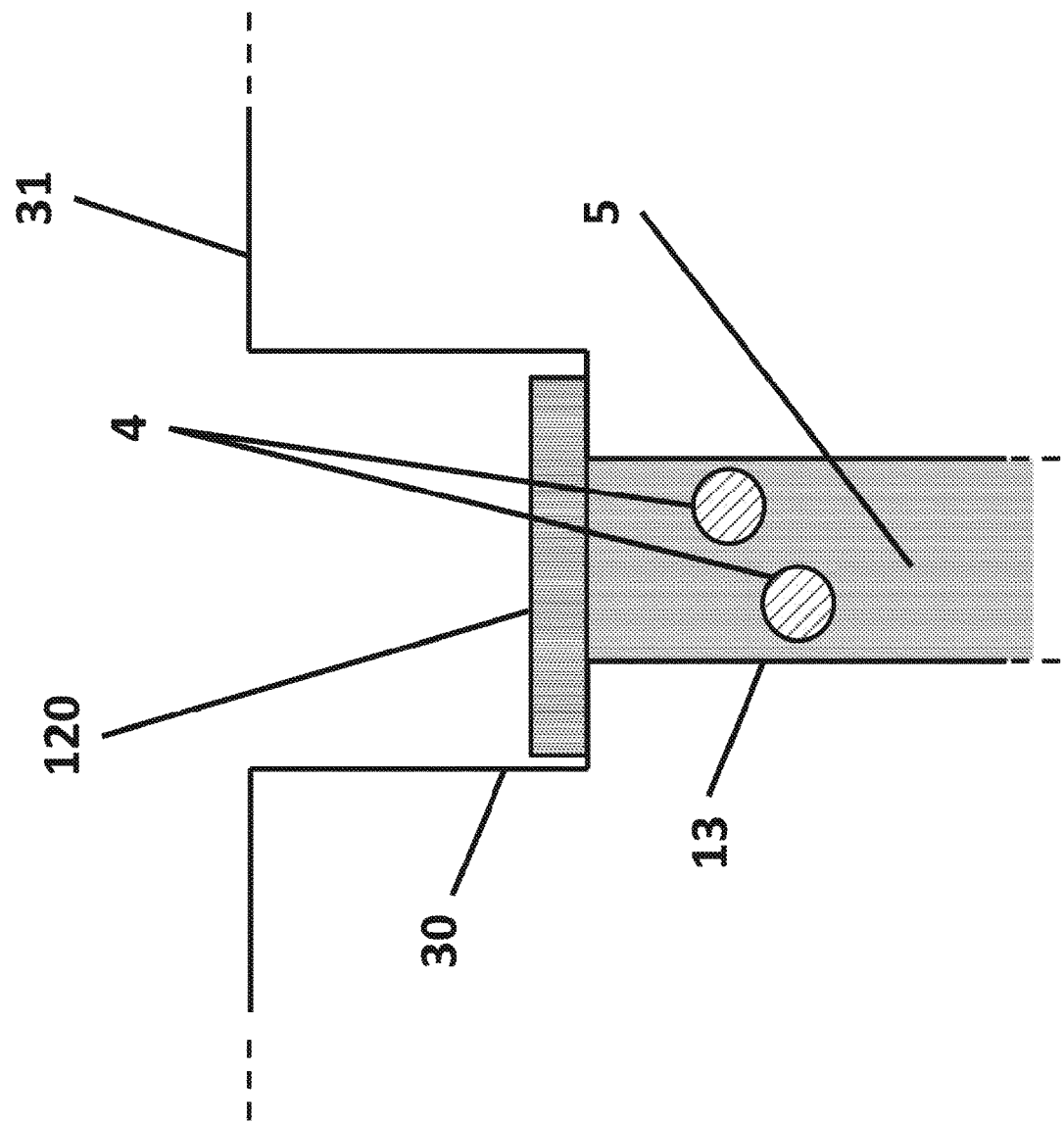
FIG. 17B is a cross sectional side view of a flow stop 120 that has hermetically sealed the top of the sedimentation capillary 13 after the aqueous sample 5 has dissolved the dry sphere 3 and released the particles 4.

FIGS. 17A and B present cross sectional side views of a passive unidirectional valve that can seal the sedimentation capillary 13 once the aqueous sample dissolves the dry sphere 3 by blocking the flow of air or fluid through the top of the sedimentation capillary 13. A flow stop 120 can be placed above the dry sphere 3. While the dry sphere 3 remains dry, the flow stop 120 cannot seal the sedimentation capillary 3 and can allow air and fluid to move through the top of the sedimentation capillary 13 (FIG. 17A). Once the dry sphere 3 dissolves, the flow stop 120 can drop down vertically or through other mechanism seal the top of the sedimentation capillary (FIG. 17B) and prevent or impede air or other fluid flowing through the top of the sedimentation capillary 13.

The flow stop 120 can be any shape that creates a hermetic seal or high impedance seal with the top of the sedimentation capillary 13 or to create a hermetic seal or high impedance inside the sedimentation capillary 13. For example, the flow stop 120 can fit flush with the top or inner sidewall of the sedimentation capillary 13. The flow stop 120 can be shaped to allow a small amount of air or fluid through. The flow stop 120 can use the surface tension from a vapor seal to seal the top of the sedimentation capillary 13.

The flow stop 120 can be sized such that is cannot tilt or move inside the cuvette or the sedimentation capillary 13 before the dry sphere dissolves. It can be light-weight such that the weight of flow stop 120 does not crush the dry sphere 3 during use, in manufacturing or transportation. The flow stop 120 can be transparent or translucent to allow light to pass through it into the sedimentation capillary 13.

Another example of a passive unidirectional valve is an air opening 51. The air opening 51 can be a small diameter capillary or small diameter opening (i.e. less than 1 mm, or less than 0.1 mm, or less than 0.01 mm, or less than 1 um, or less than 1 nm) and can be placed at the top of the sedimentation capillary 13 or at the top of the cuvette 30 or in the cover 50. The air opening 51 can allow the air or aqueous fluid through but will not allow the aqueous fluid back out. The air opening 51 can block the fluid from exiting by capillary force if the effective diameter of the air opening 51 is small enough. The air opening 51 can be coated with a material that reacts with the aqueous sample to constrict the air opening 51 or seal it altogether The surface 7 of the chip 9 can be coated with a thin optically transparent reagent adhesion layer. The protein adhesion layer can consist of gold, silver, chrome, polymer, silicon dioxide, polyimide or silicon nitride. The reagent adhesion layer can be thermally deposited, chemically deposited or spun on, or other method. The reagent adhesion layer can be less than 50 nm or less than 25 nm or less than 20 nm or less than 15 nm or less than 10 nm or less than 5 nm or less than 3 nm or less than 1 nm. For proper adhesion to silicon or silicon dioxide of the reagent adhesion layer, an additional adhesion layer of chromium or titanium can be used. The additional adhesion layer can be optically transparent and can be less than 50 nm or less than 25 nm or less than 20 nm or less than 15 nm or less than 10 nm or less than 5 nm or less than 3 nm or less than 1 nm. The reagent adhesion layer can be coated with streptavidin by passive adsorption. Biotinylated anti-bodies can be bound to the streptavidin. The reagent adhesion layer can be deposited over the entire chip, or the sensing area or localized on the individual sensors. The reagent adhesion layer can be deposited after the IC has been assembled onto the PCB to eliminate any contamination that occurred during the manufacturing process.

To minimize power dissipation and heat generation, the separation conductors can be implemented in thick top metal (top metallization having a deposition thickness greater than 1 um, or greater than 2 um or greater than 3 um). To eliminate the topology from the thick top metal can affect the assay performance, the surface can be chemically mechanically polished (CMPed). Openings in the top metal for illuminating the optical sensors below can be used to collimate the light for improved detection SNR. The increased thickness of the top metal could increase the SNR despite the increased distance from the particle to the optical sensor.

The platform described herein can be used for applications including, but not limited to, diagnostics such as simplex assays, parallel or multiplexed assays, DNA microarray assays, glucose, cholesterol, metabolites, and small molecules detection; environmental assays such as for food contamination, and water and/or soil contamination; proteomics such as protein-protein binding force measurements, protein-protein binding resonant frequencies, protein kinetics research; genomics such as DNA methylation profile, and DNA force measurements; magnetic particle 4 atomic force microscopy (AFM) such as low 1/f noise AFM, AFM with digitally controlled force and frequency, and multiplexed AFM; Magnetic Particle Characterization such as exploration of magnetic properties of particles of different sizes and characteristics; Low Cost Bio-sensor Networks such as integrated and direct wireless transmission of assay results, and real-time outbreak and/or contamination monitoring; and any combinations thereof.

Variations of the systems, devices and methods have been shown and described herein by way of example only. Variations, changes, and substitutions can occur. For example, the methods can be performed with any one or more elements of the methods absent, and any one or more element of the devices can be omitted. Various alternatives and combinations of elements between the variations described herein may be employed. All publications, patents, and patent applications mentioned in this specification are herein incorporated by reference to the same extent as if each individual publication, patent, or patent application was specifically and individually indicated to be incorporated by reference.

We claim:

1. A method of transmitting information from a stand-alone medical device to a secondary mobile device comprising:
   displaying the information in encrypted or un-encrypted format on a digital display encapsulated in the stand-alone medical device;
   recording a photograph and/or video of the digital display using a secondary mobile device;
   processing the photograph and/or video of the digital display to retrieve the information, wherein the processing is performed by a medical software application on the secondary mobile device; and
   prompting a user for a patient ID or retrieving the patient ID from login information, wherein the prompting is performed by the medical software application; wherein the information is bound to the patient ID in a HIPAA compliant manner.

2. The method of claim 1, further comprising performing a biological or chemical assay on an aqueous sample by the stand-alone medical device, and wherein the stand-alone medical device comprises an assay system.

3. The method of claim 2, wherein the presence of a target analyte in the aqueous samples is detected and/or the concentration of the target analyte is quantified.

4. The method of claim 3, wherein the number of magnetic particles specifically bound to the surface of an IC represents the concentration of the target analyte in the biological sample presented.

5. The method of claim 1, wherein the digital display displays a portion or all of the information as a one dimensional bar code or 2 dimensional QR code or other machine-readable format.

6. The method of claim 1, further comprising storing the information on the secondary mobile device and graphing the information, wherein the storing and the graphing are performed by the medical software application.

7. The method of claim 1, wherein the medical software application combines the information with historical medical information.

8. The method of claim 1, wherein the medical software application can prompt the user to contact a doctor, counselor, insurance company representative, drug company representative, clinical trial representative, a reporting agency or other third party.

9. The method of claim 1, wherein the medical software application combines the information with other information found on the secondary wireless device, such as time of day, location, login information, contact to healthcare professionals, emergency contacts, age and sex of patient or other information stored on the secondary mobile device.

10. The method of claim 1, wherein the medical software application transmits all or part of the information to a third device.

11. The method of claim 10, the medical software application omits the patient ID when transmitting information to a third device.

12. The method of claim 10, wherein the stand-alone medical device provides multiple different sets of results, wherein a first set of information is displayed on the digital display and wherein a second set of results is transmitted to a third device.

13. The method of claim 10, wherein the stand-alone medical device transmits the information to a third device for review without displaying the information on the digital display.

14. The method of claim 10, wherein the information is encrypted in a manner that can only be decrypted by a third device.

* * * * *